(12) United States Patent
Holmin et al.

(10) Patent No.: US 8,876,792 B2
(45) Date of Patent: Nov. 4, 2014

(54) ENDOLUMINAL MEDICAL ACCESS DEVICE

(75) Inventors: Staffan Holmin, Stockholm (SE); Stefan Jonsson, Taby (SE); Johan Lundberg, Danderyd (SE)

(73) Assignee: Karolinska Institutet Innovations AB, Solna (SE)

( * ) Notice: Subject to any disclaimer, the term of this patent is extended or adjusted under 35 U.S.C. 154(b) by 1060 days.

(21) Appl. No.: 12/936,825

(22) PCT Filed: Apr. 8, 2009

(86) PCT No.: PCT/EP2009/054273
§ 371 (c)(1), (2), (4) Date: Oct. 7, 2010

(87) PCT Pub. No.: WO2009/124990
PCT Pub. Date: Oct. 15, 2009

(65) Prior Publication Data
US 2011/0034828 A1     Feb. 10, 2011

Related U.S. Application Data

(60) Provisional application No. 61/043,337, filed on Apr. 8, 2008.

(30) Foreign Application Priority Data

Apr. 8, 2008  (SE) ...................................... 0800787

(51) Int. Cl.
*A61M 31/00*     (2006.01)
(Continued)

(52) U.S. Cl.
CPC .... *A61M 25/0068* (2013.01); *A16B 2017/3492* (2013.01); *A61B 17/3494* (2013.01);
(Continued)

(58) Field of Classification Search
CPC ..................... A61M 25/0069; A61M 25/0084; A61M 25/06; A61M 2025/00421
USPC .......................... 604/117, 272, 506–508, 522
See application file for complete search history.

(56) References Cited

U.S. PATENT DOCUMENTS 3,888,249 A    6/1975   Spencer
4,705,501 A   11/1987   Wigness et al.
(Continued)

FOREIGN PATENT DOCUMENTS

WO    WO 9944656    9/1999
WO    WO 99/49773   10/1999
(Continued)

OTHER PUBLICATIONS

International-type Search Report mailed Apr. 8, 2008 for Swedish Application 0800787-4.
(Continued)

*Primary Examiner* — Theodore Stigell
(74) *Attorney, Agent, or Firm* — Knobbe, Martens, Olson & Bear, LLP

(57) ABSTRACT

An endoluminal medical access device (1) is disclosed that is devised for endoluminal delivery to an extravascular target site (5) at a vasculature site of a human or animal body vasculature, such as the microvasculature. The device (1) comprises a hollow body (112) arranged around a continuous channel (113) that ends in a distal end (100) and comprises a distal penetration portion (102) that is devised to extend across a tissue wall of said microvasculature said microvasculature site (4) at an extravascular target site in said body to provide communication with said extravascular target site through said channel (113) and devised for at least partly apposition to said tissue wall, and a proximal connection section (101), which proximally adjoins said penetration portion (102), and optionally comprises an intrusion depth limit unit (116, 118) and/or a hollow separation section (115) devised to provide a controllable separation of the penetration portion (102) from a connected proximal portion (110) of the hollow body.

25 Claims, 16 Drawing Sheets

(51) Int. Cl.
  *A61M 25/00* (2006.01)
  *A61B 17/34* (2006.01)
  *A61N 1/05* (2006.01)
  *A61B 18/18* (2006.01)
  *A61M 25/06* (2006.01)

(52) U.S. Cl.
  CPC ........... *A61N 1/05* (2013.01); *A61B 2018/1892* (2013.01); *A61M 25/06* (2013.01); *A61M 25/0069* (2013.01); *A61M 25/0084* (2013.01); *A61M 2025/0042* (2013.01); *A61M 25/0082* (2013.01)
  USPC ............ 604/506; 604/117; 604/272; 604/522

(56) References Cited

U.S. PATENT DOCUMENTS

| | | | |
|---|---|---|---|
| 5,092,848 | A | 3/1992 | Deciutiis |
| 6,302,870 | B1 | 10/2001 | Jacobsen et al. |
| 2003/0078562 | A1 | 4/2003 | Makaower et al. |
| 2004/0220536 | A1 | 11/2004 | VanTassel et al. |
| 2004/0225279 | A1* | 11/2004 | Raymond ................. 604/523 |
| 2007/0225678 | A1 | 9/2007 | Lui |
| 2007/0282267 | A1 | 12/2007 | Schatz |
| 2009/0227892 | A1 | 9/2009 | Krombach et al. |

FOREIGN PATENT DOCUMENTS

| | | |
|---|---|---|
| WO | WO 99/49926 | 10/1999 |
| WO | WO 0013728 | 3/2000 |
| WO | WO 00/66199 | 11/2000 |
| WO | WO 01/45548 | 6/2001 |
| WO | WO 0176682 | 10/2001 |
| WO | WO 0189606 | 11/2001 |
| WO | WO 02/56937 | 1/2002 |
| WO | WO 02/056937 | 7/2002 |
| WO | WO 03/006089 | 1/2003 |
| WO | WO 03/009884 | 2/2003 |
| WO | WO 2005112573 | 12/2005 |
| WO | WO 2007/121143 | 10/2007 |
| WO | WO 2007121143 | 10/2007 |
| WO | WO 2007/131516 | 11/2007 |

OTHER PUBLICATIONS

International Search Report and Written Opinion of the International Searching Authority for International Application No. PCT/EP2009/054273 mailed Jun. 24, 2009.

European Search Report for Application No. 13197285.3.-1506 dated Mar. 24, 2014.

* cited by examiner

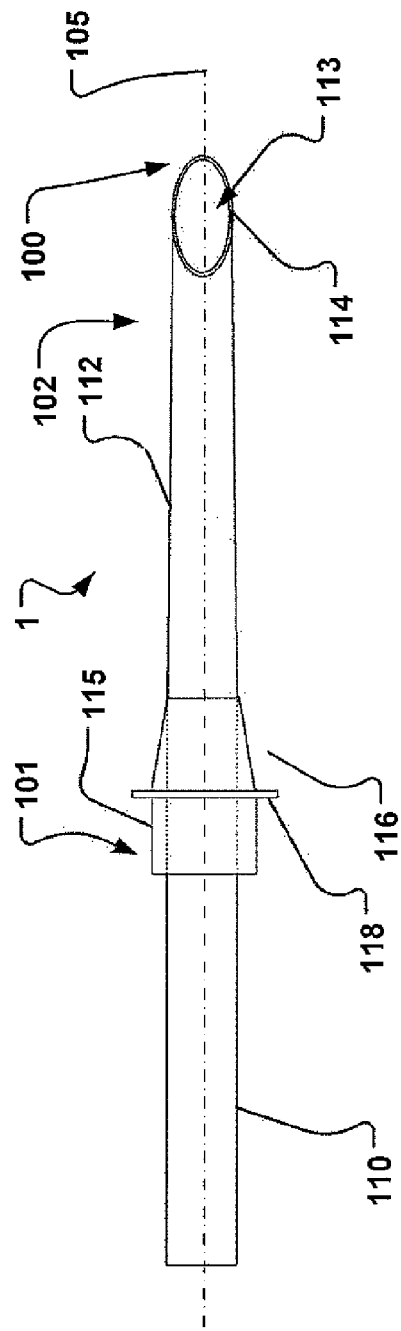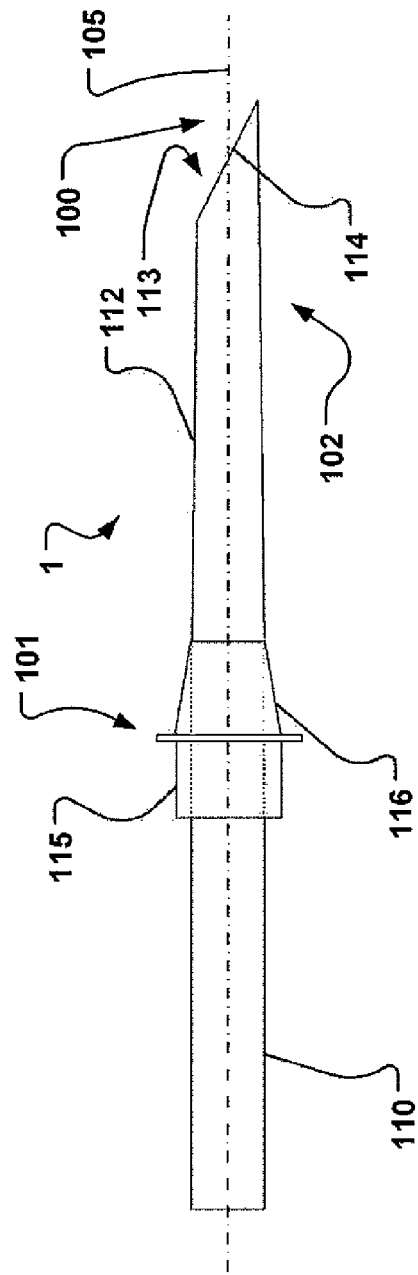

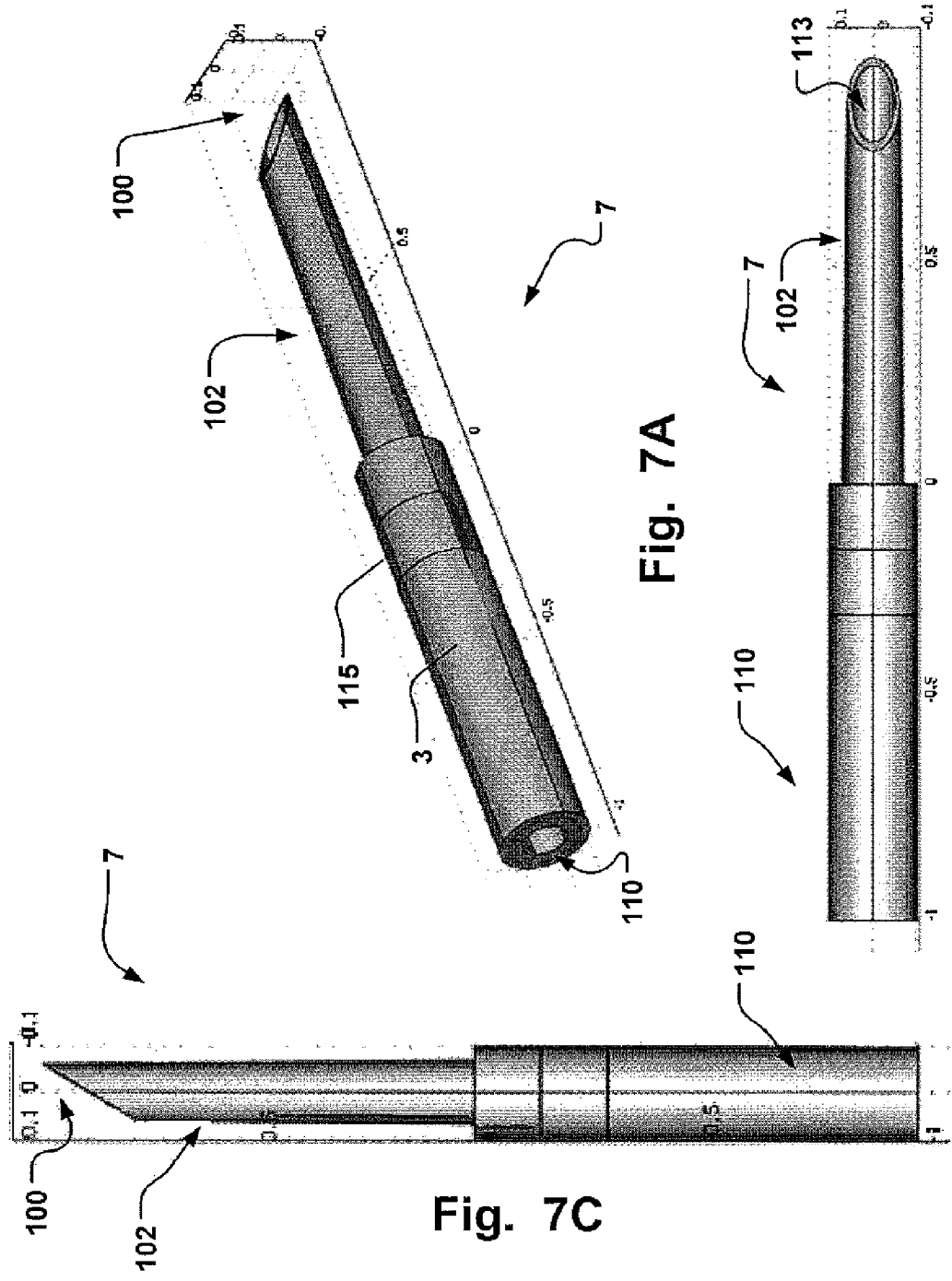

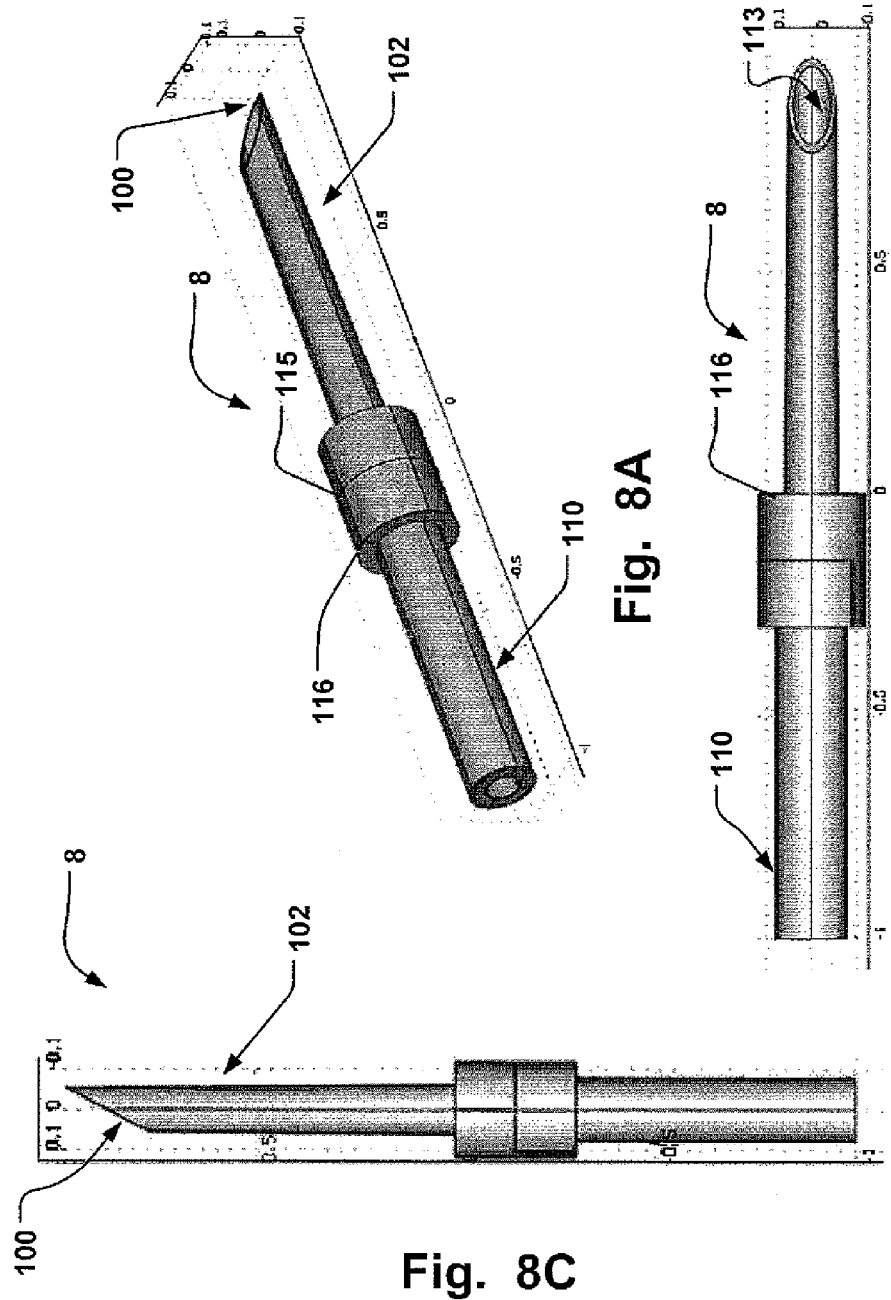

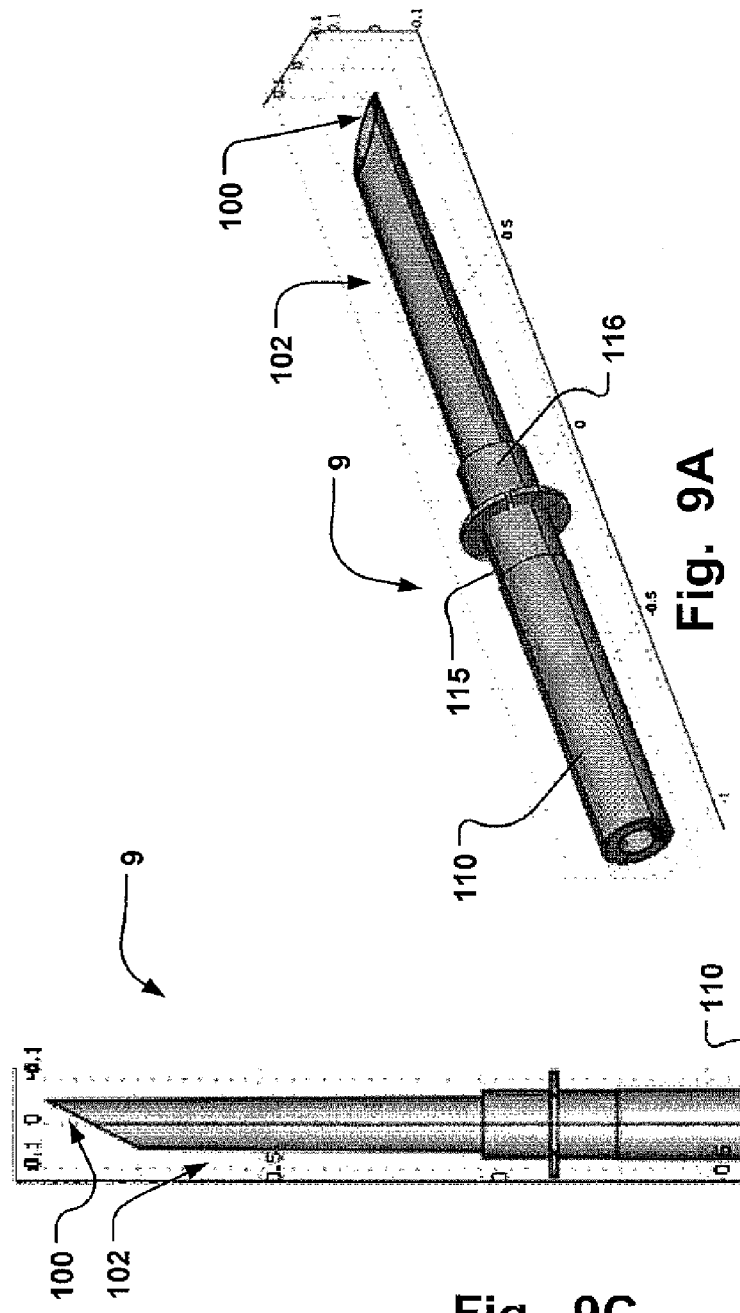
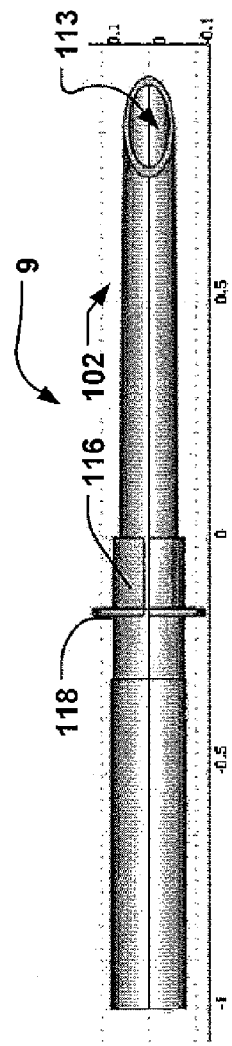
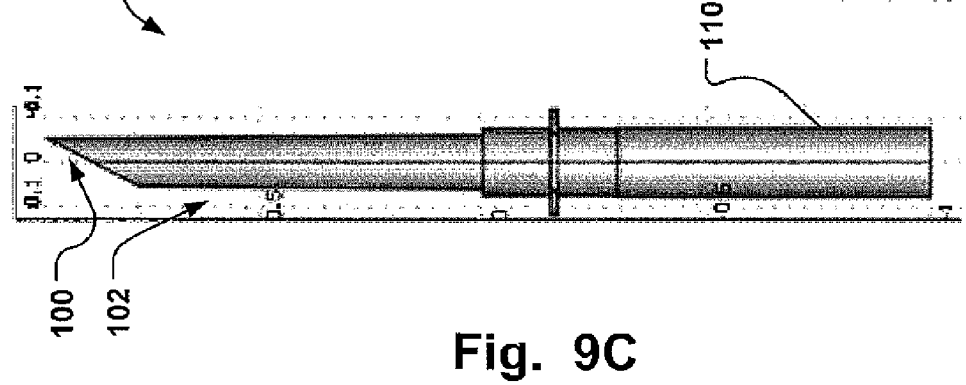
Fig. 9A
Fig. 9B
Fig. 9C

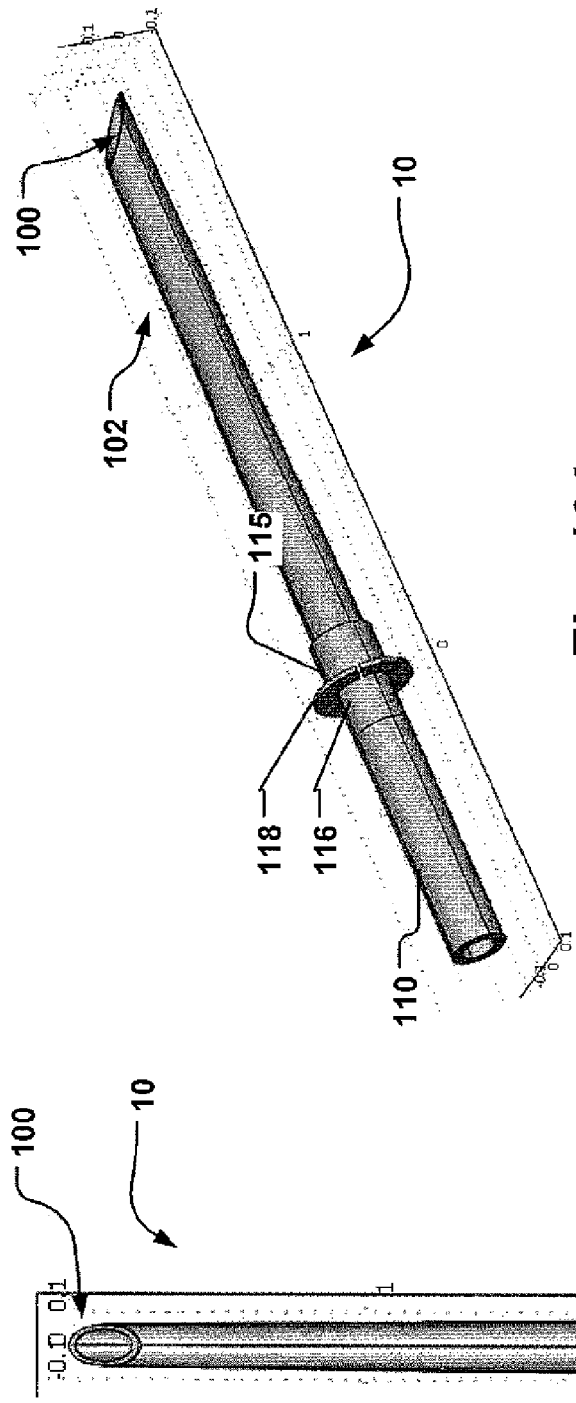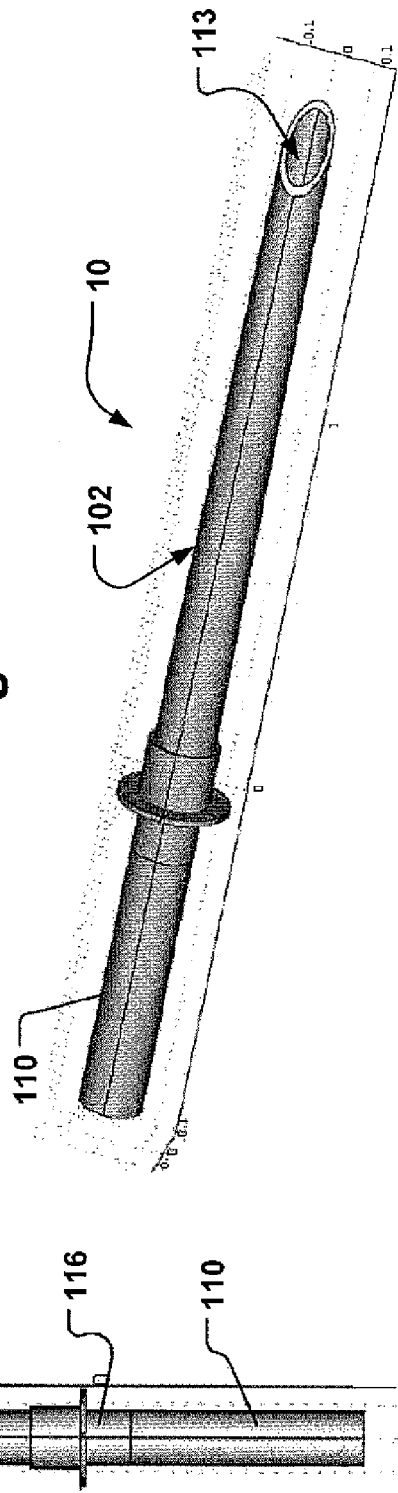
Fig. 10A
Fig. 10B
Fig. 10C

ENDOLUMINAL MEDICAL ACCESS DEVICE

RELATED APPLICATIONS

This application is a U.S. National Phase application under 35 U.S.C. §371 of International Patent Application No. PCT/EP2009/054273, filed Apr. 8, 2009, and published in English on Oct. 15, 2009, which claims priority to Swedish Application No. 0800787-4, filed Apr. 8, 2008 and U.S. Application No. 61/043,337, filed Apr. 8, 2008.

FIELD OF THE INVENTION

This invention pertains to the field of catheter based medical devices. More particularly, the invention relates to hollow probes having a piercing tip. Even more particularly, the invention relates to an endoluminal vascular medical access device for endoluminal delivery of substances to and/or from a vasculature site of a human or animal body and access to an extravascular target site located outside of the lumen of the vasculature at said site. The vascular site may be a microvasculature site.

BACKGROUND OF THE INVENTION

There is today a trend towards minimally invasive techniques for administration or sampling of substances or cells to or from various organ systems. Most organs and tissues in the body can be reached by needles with or without ultrasonic or computerized tomography guidance and if this is not possible, open surgery is an option. Stereotactic delivery, assisted by modern imaging techniques, are also existing alternatives.

However, these techniques are not applicable for all organ systems, e.g. due to the limited resolution of the imaging modalities and sub-sequential planning of safe route at justifiable patient risk and radiation doses.

Moreover, there are some target areas in the body that are not accessible by known minimally invasive techniques and devices via safe routes. For such organs with less accessible anatomical location, parenchymal access can be associated with significant surgical risks.

The development of endovascular microcatheter techniques during the last years has opened a possibility to reach parts of the body that have been difficult to reach previously by conventional means by using arteries and veins as via the "internal routes" that they constitute. The potential of these techniques was recognized due to the possibility to do minimally invasive transplantations, such as disclosed in Bliss, T., R. Guzman, et al. (2007). "Cell transplantation therapy for stroke." Stroke 38(2 Suppl): 817-26.

U.S. Pat. No. 6,602,241 of Transvascular Inc. discloses methods and apparatus for delivery of substances or apparatus to target sites located outside blood vessels. A vessel wall penetrating catheter is disclosed that is inserted into the vasculature, positioned and oriented within a blood vessel near a target extravascular site and a penetrator is advanced from the catheter so as to perform an outward penetration through the wall of the blood vessel in the direction of the target site. Thereafter, a delivery catheter is passed through a lumen of the penetrator to the target site. A desired substance or apparatus is then delivered to or obtained from the target site. In some applications, the penetrator may be retracted into the vessel wall penetrating catheter and the vessel wall penetrating catheter may be removed, leaving the delivery catheter in place for chronic or continuous delivery of substance(s) to and/or obtaining of information or samples from the target site. Alternatively, a delivery catheter having an occlusion member or balloon may be advanced into a vein or venule and the occlusion member or balloon may be used to occlude the lumen of the vein or venule during and after injection of a substance through the catheter, such that the substance will not be carried away by normal venous blood flow and will remain in the vein or venule for a sufficient period of time to have its intended effect, e.g. to enter adjacent tissues through capillary beds drained by that vein or venule.

However, the disclosure of U.S. Pat. No. 6,602,241 describes a system providing penetration of a vein, i.e. the low pressure side of the vasculature, leaving a catheter in position at the penetration site of the vein. The catheter is connected all the way through the vasculature to the entry point into the body or vasculature.

In addition, it appears that the system disclosed in U.S. Pat. No. 6,602,241 does not provide a satisfactory solution to avoid bleeding at the penetration side inside the body after completed treatment when the catheter is retracted. It is mentioned that a backflow of injected fluid may be prevented by injecting a suitable adhesive or embolizing material such as a cyanoacrylate, polyethylene glycol, hydrogel or fibrin glue through the catheter lumen as the catheter is being pulled back through the tissue tract, through which it was initially inserted.

However, this solution to avoid bleeding at the penetration site is not satisfactory from a clinical point of view as it is difficult to perform and to monitor the success thereof. In addition, the injection of adhesive or embolization material may induce thrombotic embolies or unintentionally occlude the delivery vessel completely. Furthermore, the use of adhesives is not feasible in arterial vessels due to the existing higher blood pressure pushing the adhesive material out of the penetration site into the surrounding tissue before the penetration site is closed.

Moreover, the vessel wall penetrating catheter disclosed in U.S. Pat. No. 6,602,241 is of such large size that it cannot navigate into the microvasculature, e.g. into the central nervous system (CNS). Furthermore, the vessel wall penetrating catheter body includes a rigid proximal section and an elongated flexible distal section joined to the proximal section, wherein the distal section is sized to be received within the coronary sinus (venous system). The catheter body also has a penetrator lumen accommodating a vessel wall penetrator, such as a hollow Nitinol (NiTi—an alloy of Nickel and Titanium) needle, advanceable out of a side exit port. The catheter body also has a guidewire lumen which extends to the distal end of the catheter body. In summary, the catheter comprises many components and is therefore of the aforementioned large size.

Hence, the vessel penetrating catheter disclosed in U.S. Pat. No. 6,602,241 is not suited for vascular navigation into the CNS or other similar small vessels in the body. The vessel wall penetrator body is, amongst other things due to the multi lumen design, so large that it would occlude such small vessels, which is highly undesired, and may be fatal to the CNS parenchyma supported by such an artery.

Other known techniques using stent connections between vessels comprise transjugular intrahepatic portosystemic shunts (TIPS), which is a technique to provide a permanent stent connection between large veins of the liver, e.g. the v. porta and the v. hepatic. This is an endovascular technique, using a radiologic procedure to place a stent in the middle of the liver to reroute the blood flow. The TIPS procedure is done using intravenous sedation or general anesthesia. During the procedure, an interventional radiologist makes a tunnel through the liver with a needle, connecting the portal vein, i.e. the vein that carries blood from the digestive organs to the liver, to one of the hepatic veins, i.e. the three veins that carry blood from the liver. A metal stent is placed in this tunnel to keep the track open. However, this endovascular technique is not suited for the arterial part of the body vascular system. Furthermore, it is not suited for use in microvessels, but in large vessels. In addition, a stent is left in place for keeping a permanent communication between vessels. Moreover, in practice the radiologist usually pushes and retracts the needle several times until the second vein is hit, which implies a risk for bleedings. The amount of bleeding that can occur can sometimes be life threatening needing costly patient monitoring in intensive care.

Similar unwanted multi penetration of a vessel wall with potential patient bleeding is potential while using an apparatus as disclosed in U.S. Pat. No. 6,302,870. The apparatus comprises a plurality of laterally flexible needles for reaching body cavities. The configuration of the apparatus is such that the wall of the blood vessel juxtaposed to the site of delivery is potentially circumferential penetrated by the several needle points. As the blood vessel wall becomes perforated a rupture in the wall may occur, in particular at the arterial side of the vascular system.

A further issue is when vascular walls are penetrated, e.g. by a needle, upon retraction of the needle, a compression of the exit site is needed in order to avoid bleeding. However, often it is not possible to provide a compression of such an exit site at conventionally difficult accessible target sites in a human or animal body.

Various needle tips may be found for example as disclosed in WO00/13728 or U.S. Pat. No. 5,092,848. Commonly these have in common the ability to penetrate into soft tissue and are disclosed to be permanently secured to the distal end of a delivery catheter. As the catheter is retracted the tip follows back with the catheter, leaving a transmural hole which hopefully will collapse sealing the channel in the vessel wall to the extravascular space. However, the ability to seal properly depends on e.g. the compliance of the tissue and the blood pressure in the vessel. A self sealing ability is not sufficient on the arterial side of the vascular system especially in areas where no bleeding is tolerated, e.g. in connection with CNS interventions.

Conventionally difficult accessible target sites in the body may not be reached with the aforementioned devices.

Hence, it is difficult to deliver substances to and/or from conventionally difficult accessible target sites in a human or animal body.

Microcatheters are for instance disclosed in WO03080167A2. However, a penetration of vessel walls is not anticipated or implementable with this type of microcatheter as the distal tip of the disclosed microcatheter is blunt, and the distal end portion is in addition flexible and has spiral cuts. This provides for a vascular navigation to target sites which are located far more remote in the vascular system than accessible with catheter based techniques aimed for transvascular access such as the technique disclosed in U.S. Pat. No. 6,602,241. Thus, extravascular target sites are not accessible for this kind of microcatheters.

Another microcatheter device disclosed in WO2007121143 has a tissue penetrating tip member. This device appears to be not suited for use in the microvasculature. The tip is constructed with electrodes to heat the tip facilitating advancement in the tissue. Potentially necrosis may occur. Moreover, a transluminal channel is created, which when the microcatheter is retracted, leaves a hole trough the vessel wall to the extravascular space. An undesired effect as e.g. hemorrhage, at least on the arterial side of the vascular system is likely to occur.

An issue needing a novel and inventive solution is thus delivery of substances to and/or from conventionally difficult accessible target sites in a human or animal body, such as the microvasculature, e.g. in the CNS or pancreas.

In addition, or alternatively, there is a need to provide a solution that prevents or avoids bleeding from a penetration site of a vessel wall at the target site upon completed delivery or extraction of the substances.

Furthermore, a device suitable to be used on both the venous and arterial side of the vascular system would be beneficial in the operating theater as less equipment systems would be necessary.

SUMMARY OF THE INVENTION

Accordingly, embodiments of the present invention preferably seek to mitigate, alleviate or eliminate one or more deficiencies, disadvantages or issues in the art, such as the above-identified, singly or in any combination by providing an endoluminal medical access device, a kit, and methods according to the appended patent claims.

The invention relates to an endoluminal medical access device for endoluminal delivery of substances to and/or from a vasculature site of a human or animal body and access to an extravascular target site located outside of the lumen of the vasculature at said site.

The vasculature site may be a microvasculature site, wherein microvasculature is defined as the portion of the circulatory system that is composed of the smallest vessels, such as the capillaries, arterioles, and venules.

According to a first aspect of the invention, a device is provided. The device is an endoluminal medical access device, devised for endoluminal delivery to a microvasculature site, or a vasculature site, of a human or animal body vasculature, and access to an extravascular target site at said site located outside of the lumen of the vasculature at said site. The device comprises a hollow body that is arranged around a continuous channel that ends in an opening at a distal end of the device. The hollow body comprises a distal portion that is devised to extend across a tissue wall of the microvasculature, or vasculature, at an extravascular target site in the body and devised to provide communication with the target site through the channel and devised for at least partly apposition to the tissue wall, and a proximal section, which proximally adjoins the distal portion. The distal portion is detachable or seperable from the proximal portion to be left in place at the vasculature site. The device optionally comprises an intrusion depth limiting unit.

According to a second aspect of the invention, a kit is provided. The kit comprises an endoluminal medical access device according to the first aspect of the invention, and an elongated tubular delivery device.

According to a third aspect of the invention, a method is provided. The method is a method of endoluminal access to a target site in a human or animal body, and comprises of using a device according to the first aspect of the invention. The method comprises perforating a vessel wall of the microvasculature, or vasculature, with the distal portion at an extravascular target site in the body, and positioning the distal portion for extending across the vessel wall at least partly in apposition to the tissue wall, providing communication with the target site through the channel, and detaching said distal portion from a proximal portion when a procedure is finished.

According to a further aspect of the invention, another method is provided. The method is a method of communicating with a target site in an animal or human body, comprising of establishing communication with the target site by performing the method according to the third aspect of the invention, and providing parenchymal injection of a substance, cells, fluids or other materials possible to deliver through said intervention to the target site or taking of samples from the target site through the channel.

The aspects of the invention provide for targeted substance delivery and/or sampling.

Further embodiments of the invention are defined in the dependent claims, wherein features for the second and subsequent aspects of the invention are as for the first aspect mutatis mutandis.

The medical access device is an endoluminal medical access device, herein named "extroducer" or extroducer device. The term "extroducer" is, in contrast to an "introducer", a device that is advanced from the inside of a vessel, i.e. from the inner lumen formed by the vessel, to the outside thereof. The extroducer device is advanced into the tissue of the vessel wall. The extroducer device is devised to penetrate the tissue, or alternatively or in addition, penetration may be assisted. When delivered into position through the tissue of the vessel wall, the extroducer device is providing a communication path, by an inner hollow, from the inner lumen across the tissue of the vessel wall to the extravascular space. Further, the extroducer device is distally extending into the extravascular space with a distal end thereof arranged at a target site in the extravascular space. This type of endoluminal outward delivery is described by the term "extroduced", which is an "inverted introduction" from the inside to the outside of the vessel, all inside the body. The term "extroducer" is based on this understanding. The extroducer device provides in such manner a communication channel between the inner lumen and the extravascular space. In particular embodiments, the extroducer device is devised for exiting the microvasculature from the inner lumen thereof to an extravascular target site by perforation of the lumen. The vessel for endoluminally inserting the extroducer may be any vessel throughout the body in both the arterial and the venous side. The term "extroducer" or "extroducer device" used throughout this description is contemplated being such a vascular extroducer or an 'endoluminal medical access device'.

The extroducer device provides for safely penetrating arterial or venous blood vessels with a luminal diameter, in current practical implementations down to a size of approximately 0.7 mm, to be able to administrate or sample cells and substances to/from the extravascular space at such vessels. This provides for combining minimal invasiveness of an endoluminal approach with an accurate administration in a desired anatomical target location.

For transplantation purposes, this also further provides for increasing the ratio between engrafted and transplanted cells.

Previously, in works with intravascular transplantation of cells, a control over cellular engraftment location, or a favorable ratio between transplanted and engrafted cells has not been thoroughly considered. Embodiments of the extroducer device provide for delivery of an increased ratio between engrafted and transplanted cells in a minimally invasive way.

The endovascular technique provides, at least in certain instances, such as for the CNS, the pancreas, and the heart, the merit of less invasiveness than open surgical procedures of percutaneous transplantation.

Certain embodiments of the extroducer are believed to combine favorable properties of minimal invasiveness with accurate and efficient engraftment of stem cells.

The extroducer provides for local administration of any substances, such as pharmaceutical agents, including cytostatics; growth factors or contrast. Alternatively, or in addition, the extroducer device provides for a puncture, of for example cysts, in difficult accessible anatomical locations.

The extroducer device according to some embodiments provides for a high degree of flexibility. The system is devised for delivery inside micro catheters. In embodiments the system is adapted for navigation into vessels down to 1 mm and smaller. Other embodiments are not restricted to such small vasculature dimensions. This provides for a vascular navigation to target sites which are located far more remote in the vascular system than accessible with catheter based techniques aimed for transvascular access such as the technique disclosed in U.S. Pat. No. 6,602,241. The access provided by embodiments, provides for instance for delivering of substances, cells or taking cytological preparations according to previously mentioned techniques.

The extroducer device according to some embodiments provides for arterial navigation. Some embodiments provide for venous navigation.

The extroducer device according to some embodiments provides for usability during interventions, where it is not necessary or desired to leave a catheter or fluid communication line in the vasculature, e.g. after substance delivery or finished treatment. Bleeding is avoided after finished treatment.

The extroducer device according to some embodiments comprises a communication channel devised for injection and/or aspiration purposes integrally formed with a perforation device devised for perforation of a vessel wall. This, amongst others, makes the miniaturization of the extroducer possible.

The extroducer device may provide parenchymal injection of a substance, cells, fluids or other materials, or taking of samples, even in difficult accessible anatomical locations.

The extroducer device according to some embodiments provides for a perforation of a vessel wall, wherein the perforation site in the vessel wall does not need to be plugged up upon withdrawal of the extroducer device.

Some embodiments of the extroducer device provide for devices which may be left in place in a punctured vessel wall over a period of time.

Some embodiments of the extroducer device provide for devices that are devised to seal off communication thereto at physiological pressure levels, whereby the extroducer device may be left in place in a punctured vessel wall over a period of time, wherein no leakage to or from the vessel occurs, or wherein substantially no leakage flow occurs.

Some embodiments of the extroducer device provide for devices which may be left in place in a punctured vessel wall over a period of time, wherein no or substantially no leakage or bleeding to or from the vessel occurs, and wherein the device degrades over time at the site of puncture.

A detachable distal elongate portion of the device of some embodiments may be left in place in the vessel wall at the perforation site and inherently thanks to its advantageous design prevents a flow therethrough at physiological pressures. There is no need for using an adhesive or embolization agent to close the puncture channel.

Some embodiments of the extroducer device comprise an automatic sealing. The extroducer device has such dimensions that is uses physical principles according to which a flow through the communication channel of the device does not occur at physiological blood pressure levels. This has also been demonstrated by means of in vivo experiments. Higher pressures to provide a fluid flow through the communication channel have to be provided through the connected microcatheter. The driving pressure are chosen that cells in suspension are not killed. Positive pressures provide a delivery of fluid to the target site through the communication channel of the hollow body. Negative pressures provide an aspiration from the target site through the communication channel of the hollow body.

Some embodiments of the extroducer device comprise an element for limiting the entry depth of the perforation device in tissue, e.g. a vessel wall. The limitation element may be a rigid or foldable stop element, or a recess in the outer wall of the hollow body.

Some embodiments of the extroducer device provide for a separation from the perforation device from the microcatheter. A distal portion of the hollow body is detachable and may be left in place at the target site after treatment. Thus the proximal part of the hollow body, and the microcatheter, may be retracted from the target site through the vasculature. As mentioned above, the extroducer device is devised to seal off or prevent a flow through the communication channel and may be left in the tissue. In vivo experiments has shown that the device does not return into the vessel due to positive driving pressure from the inside of the vessel vis-à-vis the extra vascular space and does not substantially travel further into tissue, ensuring patient safety.

Some embodiments of the extroducer device provide for a bioresorption or biodegradation of the device in the body when manufactured in a biodegradable material.

Some embodiments of the extroducer device provide for a clinically well acceptable and useful system.

Some embodiments of the extroducer device provide for a safe way of reaching a target site at or adjacent to a small vessel, wherein a retraction of at least a part of the device is achievable without causing bleedings or thrombotic embolies in the small vessel and without leaving behind a catheter system in the patient.

Some embodiments of the extroducer device, specifically with larger diameters, provide for devices which are sealed by advancing a sealing plug through the hollow part of the system to the distal detachable penetration device that is left in the vessel wall.

Some embodiments of the extroducer device also provide for advantageous endovascular intervention that may provide both transplantation of cells, delivering drugs, radioactive substances and other substances and sampling body fluids and cytological preparations.

Some embodiments of the extroducer device also provide for a system that in its entirety fits into current standard microcatheter systems that provide navigation capabilities and integration with currently used equipment. Embodiments of the extroducer device thus provide for quick treatment in emergency cases.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which FIG. 1 is a schematic illustration of a device according to an embodiment in a side view from above;

FIG. 2 is a schematic illustration of the device of FIG. 1 in a lateral view;

FIGS. 7A, 7B, 7C are a perspective view, a side view from above, and a lateral view of a practical implementation of an extroducer device;

FIGS. 8A, 8B, 8C are a perspective view, a side view from above, and a lateral view of another practical implementation of an extroducer device;

FIGS. 9A, 9B, 9C are a perspective view, a side view from above, and a lateral view of a further practical implementation of an extroducer device;

FIGS. 10A, 10B, 10C are a perspective view, a side view from above, and a lateral view of yet another practical implementation of an extroducer device;

DESCRIPTION OF EMBODIMENTS

Figure 3A:
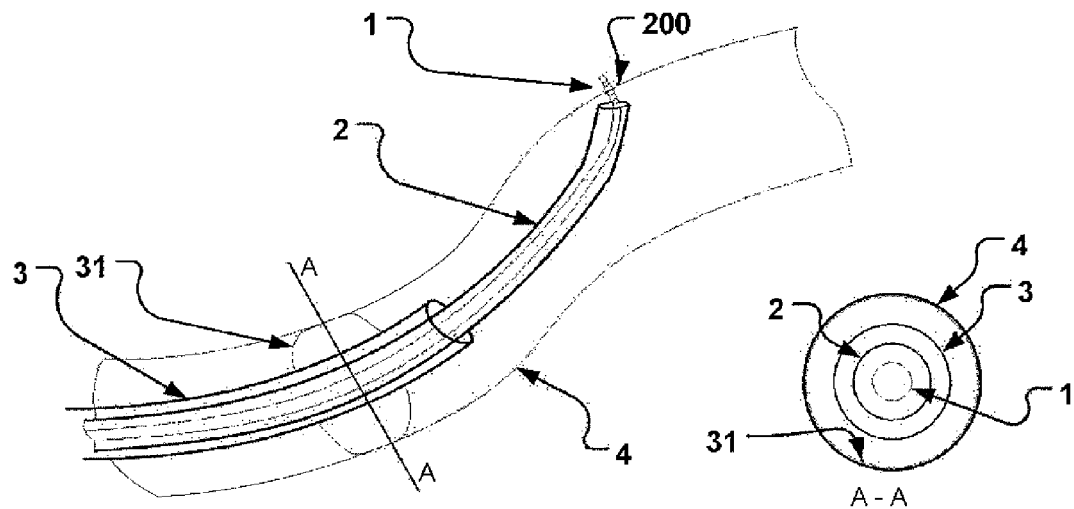
FIG. 3A is a schematic illustration of delivery of the device of FIG. 1 through the microvasculature to a target site.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Advancements in stem cell techniques have created a potential for regenerative treatments to a vast spectrum of diseases, e.g. diabetes mellitus, morbus Parkinson, ischemic heart disease, traumatic brain injury, and stroke.

Therefore there is a need for efficient and minimally invasive techniques for delivering the cells to a desired target organ and/or pathological system. Such delivery is provided by the extroducer device.

A comparison of different techniques for administration to the central nervous system (CNS) following stroke with emphasis on the sheer number of cells engrafted shows that the most efficient way of administration is intracerebral (ic) followed by intracerebroventricular (icv) and then intravenous (iv) delivery.

To make a successful transplantation of stem cells, a few considerations must be made, e.g. accessibility to a target organ, number of cells and volume of cell suspension and the engraftment success-rate. It has been argued that some cells possess an internal homing feature mediated through receptor-ligand interactions. For cells with such properties an iv route would probably be favorable giving better distribution throughout the transplantation target volume.

In situations where the cellular engraftment rate after endovascular administration is low and when a high anatomical specificity for the engraftment is required, direct puncture of the parenchyma is preferable. This was hitherto done with a percutaneous guided needle puncture or in a combination with open surgery.

However, as mentioned above, with percutaneous guided needle puncture or in a combination with open surgery, some target regions of the body, such as the CNS or the pancreas, are difficult or not at all accessible without jeopardizing patient safety, including an increased risk of e.g. morbidity, expense, trauma, patient mortality, and other complications. Hence, a system with improved patient safety would be desirable and is provided in form of the extroducer device.

The design and concept of the device of embodiments is adapted to be clinically applied according to the clinically well proven Seldinger technique, as disclosed in Seldingers original work describing the introducer, Seldinger, S. I. (1953) "Catheter replacement of the needle in percutaneous arteriography; a new technique." Acta radiol 39(5): 368-76, which is incorporated herein in its entirety for all purposes. However, there are differences between the Seldinger introducer and devices according to embodiments.

The design of the extroducer device facilitates to provide the small dimensions necessitated by the required microvasculature access to specific target sites. However, the design is also compatible and adaptable for larger dimension catheter systems, when required in specific embodiments or applications.

The extroducer devices comprise an integrated communication channel in a hollow body and a distal perforating unit in a single lumen system. Navigation through the vascular system down into microvessels, for instance of a diameter of 1 mm or smaller, is facilitated by the devices. Some embodiments are not such limited and are scaled up to use in larger vessel systems.

Some embodiments have a stop element for the perforation unit. The stop element limits intrusion depth. Intrusion depth is thus advantageously controllable without the need of high resolution (and dosage) imaging modalities. The stop element may be a protruding flange. The flange may be foldable or fixed. The stop element may also be a recess in the outer wall of the hollow body at a defined distance from the distal tip of the perforation unit. The stop element provides a defined maximum penetration depth and position in tissue upon insertion. The stop element may be integrated with an anchoring element.

Some embodiments of the devices are devised to provide an absence of fluid communication in the communication channel under physical blood pressure levels thanks to its physical dimensions. In larger vessels some embodiments might have to be sealed by advancing some form of plug through the working channel. This facilitates the use of the device even on the high pressure side of the vascular system. Bleeding at the perforation site is efficiently avoided, in small vessels without the need of a plug or other measures.

The arterial system is anatomically substantially more homogenous than the venous system and therefore it is easier to reach target sites via arteries. Conventionally, however, the arterial access path is regarded as more problematic due to the existing higher blood pressure, potentially more difficult stopped bleeding, etc.

Thanks to the extroducer devices having in embodiments an inert property to allow fluid flow through a channel in the hollow body only at driving pressures well exceeding physiological systolic blood pressures, this issue is overcome and more convenient access paths are accessible than previously feasible. Alternatively, or in addition, a stopper element, such as a stop plug may suitable be provided, e.g. in situ by delivery through the working channel or hollow body of the system in order to provide a closing off of the communication channel, e.g. in larger embodiments of the extroducer device. The stop plug may be made of a bio-compatible material like gold or silicone or tissue glue.

Some embodiments comprise a hollow separation or detachment section that provides a controllable separation of the distal portion of the hollow tube including the perforation unit from the proximal part of the device and/or the microcatheter. Thus, the proximal part and the microcatheter may be retracted from the target site through the vasculature, leaving a distal part perforated in the vessel wall. Fluid communication of the distal part may be shut off due to the dimensions of the distal part or by using a plug unit.

Applicable separation mechanisms are disclosed in WO2006/024040 which is incorporated herein by reference in its entirety for all purposes. However, the present invention differs from the disclosure of WO2006/024040 in many aspects. WO2006/024040 applies to delivery of implants, such as occlusion devices or stents in the vasculature. Applicants refer to the detachment mechanisms, which may be applied to embodiments of the extroducer device. Detachment of the proximal part of the device from the distal, penetration part may thus be implemented according to the detachment principles described in WO2006/024040. These and further embodiments of detachment units are described in more detail below.

The extroducer device may be used according to at least two alternative procedures.

In the first alternative procedure, a vessel wall, such as a microvessel wall, is perforated with a sharp tip of distal end of the extroducer device, namely the hollow penetration portion. Then the penetration portion is further inserted, through the vessel wall, such that access to the extravascular space is provided through the inner lumen of the extroducer device. An intrusion depth limiting unit may provide controlled intrusion depth of the penetration portion into the vessel tissue and extravascular space. A fluid communication through the microcatheter and through the extroducer device is thus provided with the extravascular space at the puncture site, e.g. of the microvessel. After the procedure is completed, i.e. a delivery or sampling of material to or from the extravascular space of the target site at the puncture site, the distal penetration device is then separated or detached from the proximal hollow body of the system and left in place in the tissue at the penetration site or left in place for future use. The detached distal part is then sealed off. This sealing may be provided automatically at physiological pressures, or by plugging of the inner hollow of the device, depending on the applied diameter of the inner hollow of the extroducer device.

In the second alternative procedure, penetration is made with a separate, solid or hollow elongated puncture device located inside the hollow extroducer system (not illustrated). The distal end of the extroducer device is slid over the solid or hollow elongated puncture device until it is in position. A stop element may provide an advantageous positioning in the vessel wall. Then the solid or hollow elongated puncture device is retracted, leaving the distal portion of the extroducer device punctured in position and arranged for fluid or tissue or cell-suspension communication to or from the extravascular space of the target site at the puncture site. The solid or hollow penetrating device may have a sharp tip or be compromised of an eximer laser or other cutting devices. After the procedure is completed, i.e. a delivery or sampling of material to or from extravascular space of the target site at the puncture site, the penetration device is sealed, automatically or by plugging as described in the first alternative procedure. Then the distal portion of the extroducer device is separated from the proximal portion thereof or the microcatheter. The distal portion is left in place in the tissue at the penetration site.

The extroducer device may be made of a bioresorbable or biodegradable material, such that the extroducer device is resorbed or degraded and thus eliminated from the target site over time.

Now turning to the Figures, an embodiment of the extroducer device is illustrated in FIGS. 1 and 2.

The extroducer device is an endoluminal medical access device 1, devised for endoluminal delivery to a target site, e.g. to a microvasculature 4 of a human or animal body vasculature. The device 1 comprises a hollow body 112 that is arranged around a continuous channel 113 that ends in an opening at a distal end 100 of said device. The hollow body 112 has a wall thickness defining an outer wall having a cross-section or diameter and an inner wall around the lumen or channel 113. The hollow body 112 comprises a distal elongate portion or penetration portion 102 that is devised to extend across a tissue wall 200 (see FIGS. 3A and 3B), e.g. of said microvasculature 4, at an extravascular target site 5 in said body. The distal elongate portion 102 (herein in short "distal portion") may have a sharp tip 114. The distal portion 102 may be conically tapering, as shown in the Figs., to allow for improved seating and sealing in the tissue wall 200. The conical tapering is present either along a substantial portion or the entire length of the distal portion 102, as illustrated in some of the Figs., in addition to the pointed tip portion (when present in embodiments not using an external penetrator unit) at the very distal end of the device.

The hollow body 112 has a longitudinal axis 105, and is devised to provide communication with said target site 5 through said channel 113 and devised for at least partly apposition to said tissue wall 200. A proximal connection section 101 proximally adjoins said penetration portion 102. The embodiment of device 1 comprises an intrusion depth limitation unit 116. Alternative intrusion depth limitation units are described below. In addition, the intrusion depth limitation unit 116 may be integrated with an anchoring unit, such as a barb, prong, spike, hook, etc. The latter may advantageously support later detachment, as the distal portion 102 is kept safely inserted in the vessel wall, preventing a withdrawal of the distal portion at e.g. partial detachment.

The proximal portion 110, extending from the proximal end of the endoluminal medical access device, may have a larger cross-sectional outer wall dimension (diameter in circular cross sections) and corresponding inner lumen diameter than a distal portion, extending from the distal end thereof. A transition from the larger diameter to the smaller diameter may be stepwise or continuously tapering. In this manner the distal end may navigate more flexibly to the target site, such as the microvascular site 4. For instance when navigating towards a target site in the CNS, it is sufficient that a distal portion of approximately 30 cm has a very small cross-sectional dimension, while the remaining proximal part can have a larger cross-sectional dimension/diameter. A stepwise or continuously narrowing or tapering endoluminal medical access device has an advantageous stability and torsional rigidity providing for good maneuverability of the endoluminal medical access device intravascularly.

The endoluminal medical access device 1 comprises a transition section from said distal penetration portion 102 to said proximal connection section 101, which comprises a hollow separation section 115 that is devised to provide a controllable separation of said distal (penetration) portion 102 from a connected proximal portion 110 of said hollow body.

The hollow body 112 may be made as a monolithic, integral part including the proximal portion 110 and the distal portion 102. The hollow separation section 115 may be positioned dose to a stop flange 118, or at the flange 118, such that the flange 118 bears against the vessel wall 200 upon insertion, as illustrated in FIG. 3B. In this manner no portion, or only a minor portion, of the endoluminal medical access device 1 protrudes into the microvasculature 4 upon separation, detachment or release of said distal penetration portion 102 from the proximal portion 110 of the hollow body. Range 118 may also be detached from the proximal portion 110, as in the present embodiment. In other embodiments, the flange portion may be detached from the distal penetration portion 102. The proximal portion 110 may thus be withdrawn from the punctured delivery site upon finished communication with the extravascular space of the target site at the puncture site.

The separation, detachment or release is made in a controlled manner and may be done in several ways. Releasing the distal penetration portion 102 from the proximal portion 110, at the hollow separation section 115 may be done in several ways. Separation is for instance achieved by means of electrolytic, magnetic, induction or thermal detachment. Some detachment mechanisms may for instance be thermal, as disclosed in WO2006/024040, which is fully incorporated by reference herein. The disclosure of WO2006/024040 has to be suitably modified to adapt to the present invention for hollow tube distal portion detachment.

The change in mechanical material properties of the structure of the hollow tube at the separation section 115 results in detaching the distal penetration portion 102 from the proximal portion 110.

Thermal activation, may e.g. initiated by an electrical current heating a portion of the hollow separation section 115 until separation is achieved and the proximal portion 110 can be withdrawn. An electrical current may be provided via suitable conduction along the hollow body. Conduction of electricity may be made along the hollow body, either by integrated wires or the hollow body itself. When the hollow body is made of a conductive material, it may be provided with an isolating layer along the length of the hollow body which ends at the non-isolated separation section 115. One conductor along the hollow body from the proximal end may be sufficient, in case a counter electrode is provided e.g. outside the body. Alternatively, two conductors may be provided, e.g. in the same layer of separate isolated layers that extend along the hollow body from the proximal end to the hollow separation section 115. Applying the electrical current for a pre-determined time activates the separation. Monitoring the current allows for a feedback when separation has occurred when the current drops. Alternatively, or in addition, an external power source may be used, e.g. outside the body or inside the body but remote from the penetration site. Such external power source may transmit energy by magnetic induction. Alternatively, or in addition, catheter based or endoscopic delivery of external power sources may be provided within the body to the separation section 115. Separation or detachment is provided upon delivery of energy from the external power source.

An electrolytic detachment mechanism may for some embodiments utilize reconfiguration of chemical properties in the separation section 115. By causing e.g. a locally elevated temperature, or initiating a chemical reaction which locally changes the chemical properties of the hollow separation section 115, detaching the distal penetration portion 102 may be achieved. Disintegration of a portion of the hollow separation section 115 may be initiated by removing disintegration or removing of a cover layer and exposing the separation section 115 to body fluids.

Alternatively, or in addition, spring force release may be used two provide the separation. A spring unit is thus provided at the hollow separation section 115. The spring force, when initiated, acts upon the hollow separation section 115 to achieve the separation. The spring force may for instance act upon a pre-determined breaking point or weakening in the hollow body. The weakening may be an indentation or notch in the hollow body that is chosen to be sufficient strong for normal handling during insertion and use of the channel 113. Release of the spring force may done in several ways, e.g. by a tether when drawn from the proximal end, removing a restriction unit that keeps a spring in tension until removed, dissolving a restriction unit after a predetermined time in the body, etc. The spring action may be provided axially pushing the distal penetration portion 102 away from the proximal portion 110 with a sufficient force, e.g. to disrupt the two portions from each other at the hollow separation section 115.

Alternatively, or in addition a predetermined breaking point may be provided at the hollow separation section 115. The predetermined breaking point may be activated by a sufficient high pressure from inside the hollow tube, provided from the proximal end thereof. When applying such a high pressure for a short time only, the separation is achieved by breaking the connection at the hollow separation section 115 without causing a flow or otherwise harming tissue at the target site. Separation is achieved by mechanically breaking open the hollow separation section 115.

Alternatively, or in addition, a threaded detachment may be used two provide the separation. The distal penetration portion 102 may be threaded to the proximal portion 110. Upon suitable rotation of the proximal portion 110 the two may be unscrewed from each other for separation.

Alternatively, or in addition, a cutting rotational movement of a cutter element at the hollow separation section 115 may provide for the separation, similar like a pipe cutter.

A sheath around the hollow separation section 115 may avoid damage to surrounding tissue during separation.

In summary, the hollow separation section 115 allows to withdraw the proximal portion of the hollow tube, leaving behind the distal portion inserted in the tissue through the vascular wall.

In embodiments, the endoluminal medical access device 1 comprises an intrusion depth limitation unit 116.

The intrusion depth limitation unit 116 may be an abutment unit. The abutment unit is for instance comprising the flange 118 devised to limit an intrusion depth of said endoluminal medical access device into said tissue wall upon insertion thereof.

In an embodiment the flange 118 may be foldable towards said hollow body 112.

The hollow body 112 may be tapered towards said distal end 100. This ensures that the device 1 securely is held in position in the vessel wall tissue.

Figure 11A:
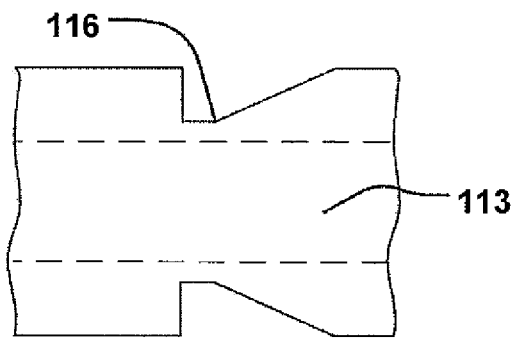
FIGS. 11A, 11B, 11C, 12A, 12B, 13A, 13B, 14A, 14B, 15A, 15B, 16A, and 16B illustrate different configurations of intrusion depth limitation units.
Figure 11B:
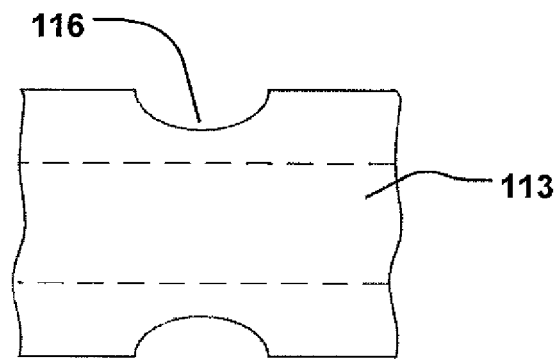

Alternatively, or in addition, the intrusion depth limitation unit 116 may be a recess in the outer wall of the hollow body, such as shown in FIGS. 11A and 11B. The recess is received in the surrounding tissue, which resiliently enters the recess and provides for an increased intrusion force holding the distal portion 102 in place when inserted into the tissue of the vessel wall.

Figure 17A:
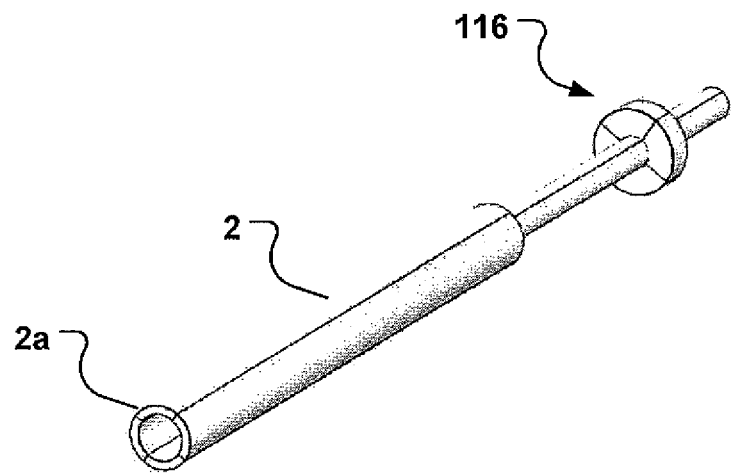
FIGS. 17A, and 17B are schematic illustrations of an extroducer device and a polymer tube 2 with a proximal intrusion depth limitation unit.
Figure 17B:
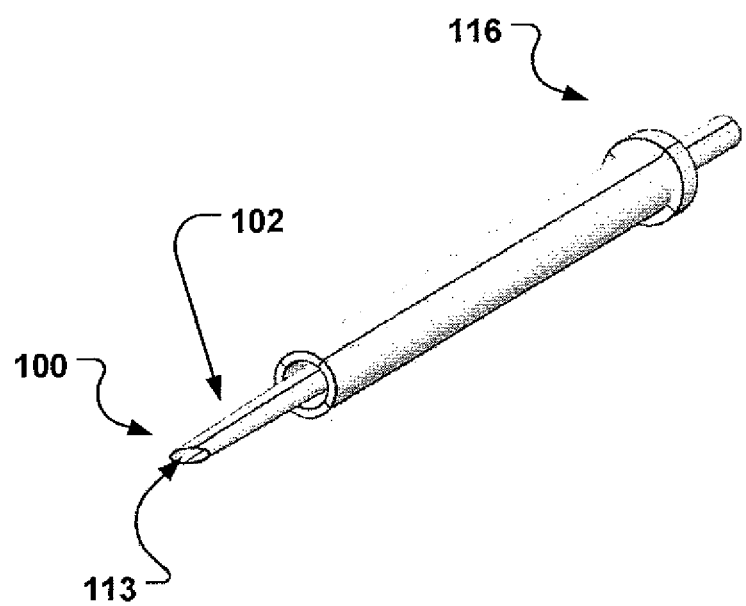

Alternatively, or in addition, an intrusion depth limitation unit 116 may be placed at the proximal end of the elongated tubular delivery device 2 (polymer tube) enclosing the extroducer device. During advancement to the target site, the extroducer device is encapsulated by the polymer tube 2, see FIG. 17A. At the target site, the extroducer device is slid inside the polymer tube 2 until stopped by the proximal intrusion depth limitation unit 116, see FIG. 17B. The vessel wall is then penetrated by the distal portion of the extroducer device until contact is established between the vessel wall and the distal end of the polymer tube. The distal end of the polymer tube acts as shoulder element. As the length of the distal portion 102 outside the distal end of the polymer tube is determined by the intrusion depth limitation unit 116, the intrusion depth of the extroducer device through the vessel wall into the extravascular space to the target site is well defined. The distal end 2a of the polymer tube 2 will then act as an intrusion depth limiting device. An advantage of the proximal position of the intrusion depth limitation unit is that the intrusion depth can be adjusted with appropriate design of the stopping mechanism, allowing for adjustments of the fixation point to the extroducer device. In case the proximal portion of the extroducer device is a microcatheter, the depth limitation unit 116 is attached to the microcatheter as illustrated in FIG. 17A. The depth limitation unit 116 is provided as a radial protruding dement, such as a flange. Attachment of the depth limitation unit 116 may be accomplished in various ways, such as adhesive attachment, friction engagement, clamping, crimping, welding, soldering, etc. When the procedure is completed, the distal portion 102 may be detached from the proximal portion of the extroducer device as described above, and the polymer tube 2a and the proximal portion of the extroducer device are retracted from the vessel and the body.

The channel 113 has such physical dimensions that it is auto sealing at physiological pressures, such that the device 1 is adapted for delivery either in an arterial or a venous side of said vasculature. Auto-sealing refers to a zero flow, or substantially zero flow, through the hollow channel 113. As for instance can be seen in the practical implementations shown in FIGS. 7-10, an inner diameter of such auto-sealing devices is approximately 0.1 mm at a channel length of approx. 1 mm. If larger dimensions of the system are used, the channel 113 may be sealed by a plug that is advanced through the hollow body 112 to the distal penetration portion 102. Sealing is advantageous to prevent bleeding when the distal portion 102 is left in place in the vessel wall after treatment.

The hollow body 112 may be a hollow tube, and a material of said hollow body 112 may be metal, such as NiTinol. Alternatively, the hollow body 112 may be made of a polymeric material. In addition, the hollow body may comprise fiducial markers, such as of a radiopaque material, such as gold, tantalum, wolfram. Such fiducial markers may for instance be positioned on the oblique tip of the penetration portion 102. In this manner a position and orientation of the device 1 is determinable by imaging units known in the art.

A material of said extroducer device or only the distal penetration portion 102 may also be a bioresorbable or biodegradable material.

Figure 3B:
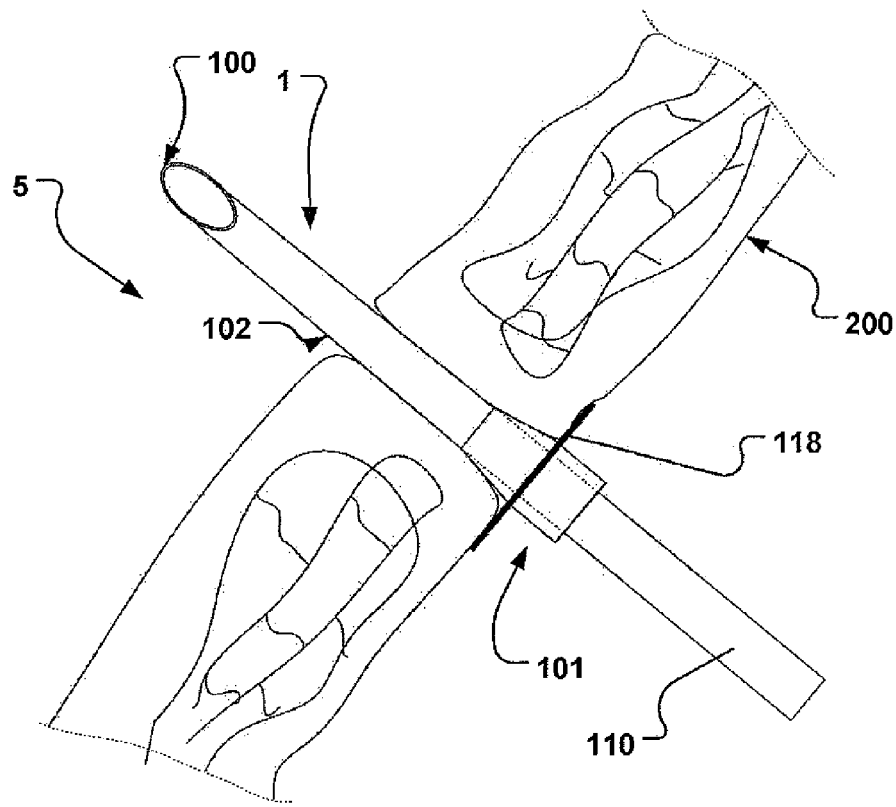
FIG. 3B is a schematic illustration of the device of FIG. 1 in penetration of a vascular wall.

Now turning to FIG. 3A, the device 1 of FIG. 1 is illustrated in a position delivered through the microvasculature to a target site 5. FIG. 3B gives a more detailed view of the penetration site of the vascular wall 200. It should be noted that the wall thickness of the vessel wall 200 is not shown to scale for illustrative purposes. The vessel wall 200 has a thickness that is substantially smaller than the length of the hollow body 112.

In a kit an endoluminal medical access device 1 is comprised, as well as an elongated tubular delivery device 2. The elongated tubular delivery device 2 may be provided in form of a tubing of polymeric material arranged coaxially around said endoluminal medical access device 1, thus providing a first assembly. The medical access device 1 is arranged for sliding motion in said elongated tubular delivery device 2.

The first assembly is coaxially and arranged for sliding motion in a microcatheter 3, providing a second assembly. The microcatheter 3 may for instance be a microcatheter as disclosed in WO03080167A2. The microcatheter may be of standard types with or without a distal balloon mounted on the outside of the working channel.

The second assembly may be coaxially and arranged for sliding motion in a conventional catheter, for delivery in vessels of a diameter down to approximately 1 mm. When the conventional catheter is at the target site, the microcatheter is advanced towards the microvasculature or the vessel wall, and the extroducer device 1 is advanced in the tube of the first assembly towards the target site 5. The microcatheter 3 (and/or the conventional catheter) may comprise an inflatable balloon 31 mounted on the outside of the working channel for fixation of the microcatheter or conventional catheter to the surrounding vessel, as shown in FIG. 3A. The distal tip of the microcatheter 3 may be angled to point radially outwards, towards the interior of vessel wall 200. At the target site, the extroducer device 1 is pushed out of the elongated tubular delivery device 2 and thus penetrates the vessel wall 200. Alternatively, a separate penetrator device may be used, as mentioned above.

Thus endoluminal access is provided to an extravascular target site 5 in a human or animal body by using an extroducer device 1 from inside the vasculature through the vessel wall. In more detail, the extroducer device 1 perforates and/or bridges the vessel wall 200 of said microvasculature 4 with said penetration portion 102 at the extravascular target site 5 in said body. The penetration portion 102 is positioned such that it is extending across said vessel wall 200 at least partly in apposition to said tissue wall 200. Thus communication with said target site 5 is provided through said channel 113. Fluid flow may be provided through the channel from the proximal section 110 to or from the distal end 100 of the device 1 through the channel 113.

Communicating with the target site 5 may thus be provided by establishing communication with said target site 5 by performing the above described endoluminal access method. Delivery of a substance to said target site 5 or taking of a sample from said target site 5 may thus be provided or performed through said channel 113. The substance may comprise cells, such as stem cells, thus providing endovascularly transplanting said cells into said target site 5.

The delivery of said substance may comprise local administration of said substances, such as cytostatics, contrast or growth factors. The substances may also include radioactive agents, such as radioactive isotope particles.

The substances may be delivered to a target site by means of the present device upon puncture. The puncture may comprise, except puncturing a vessel wall, a puncturing of a cyst for delivery of substances to the interior of said cyst for treatment thereof.

The taking of said sample comprises a puncture, of for example a cyst and providing communication to the interior of said cyst by the present device.

The method may further comprise subintimally passing an occlusion or stenosis of a vessel. The intima is the inner layer of the wall of an artery or vein. The hollow body 112 may be at least partly passed within the intima along the vessel wall 200, at an oblique angle, in contrast to the illustration of FIG. 3B, where the vessel wall 200 is penetrated perpendicularly.

The target site 5 may be located and accessed in difficult accessible organs or areas of the body, such as for instance the Central Nervous System (CNS), the pancreas, the heart, or the like, but is not restricted to these organs.

One possible application of the endoluminal medical access device is in connection with cardiac indications, such as myocardial infarction or cardiomyopathy, or the like. The endoluminal medical access device may be delivered via the coronary arteries or veins, which supply a diseased portion of the heart, to a vascular site at the diseased portion of the heart. The endoluminal medical access device is then used to penetrate the vessel wall at the vascular site in order to gain access to the treatment site of the diseased portion of the heart. In this manner substances like cells, growth factors, or other agents may be delivered in order to ameliorate cardiac function.

Figure 4A:
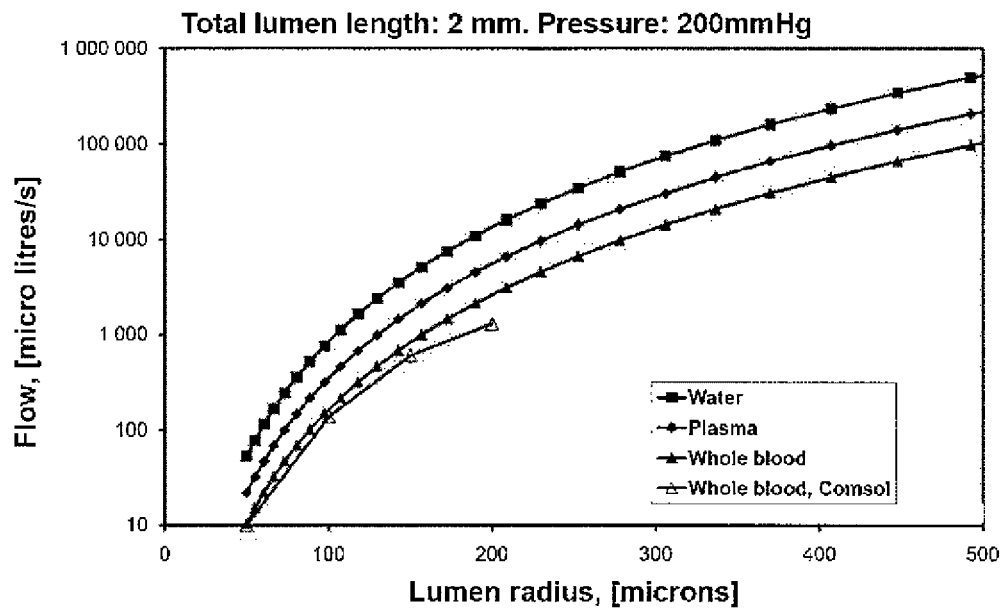
FIG. 4a is a graph illustrating a circular Poiseuille flow through a practical implementation of an extroducer device.

FIG. 4a is a graph illustrating a circular Poiseuille flow, filled symbols, driven by a pressure of 200 mmHg through a practical implementation of a device according to an embodiment of 2 mm lumen length and various lumen radii, wherein the flow rates of water, plasma and whole blood at 37° C. and a physiological hematocrit of 45 (Y-axis) are plotted against the lumen radius (X-axis) in a logarithmical way. The calculations were done in accordance with the detailed description in [James E. Fay, Introduction to Fluid Mechanics, MIT Press, 1994, p 288.]. The viscosity of water at 37° C., 6.17E-04 Pa·s was taken from the same source (p. 17) whereas the viscosity of plasma, 1.5E-03 Pa·s and the viscosity of whole blood at 37° C. and a physiological hematocrit of 45, 3.2E-03 Pa·s, were taken from [http://ima.epfl.ch/~steiner/documents/Cours/Genie_Medical/VISCOSITY.pdf]. According to fluid mechanics, the flow rate out of the lumen varies as the fourth power of the radius. Consequently, the flow rate becomes very small very rapidly as the lumen radius is reduced, which is clearly illustrated in FIG. 4. Calculations for whole blood at 37° C. and a physiological hematocrit of 45 were also performed using a commercial available product, COMSOL Multiphysics, open symbols. At a radius of 50 micrometer, the results of the two methods coincide but at higher radii, the open symbols show lower flow rates because of turbulent flow, taken into account in the calculations with COMSOL Multiphysics. The flow velocity rates determinable from the graph correspond to those of some embodiments of the extroducer device described herein. The auto-sealing effect at physiological pressures of some embodiments of the extroducer device becomes apparent from the graph in FIG. 4a when taking into consideration the inert property of blood to coagulate at low and/or turbulent flow. At least substantially no leakage flow occurs.

Figure 4B:
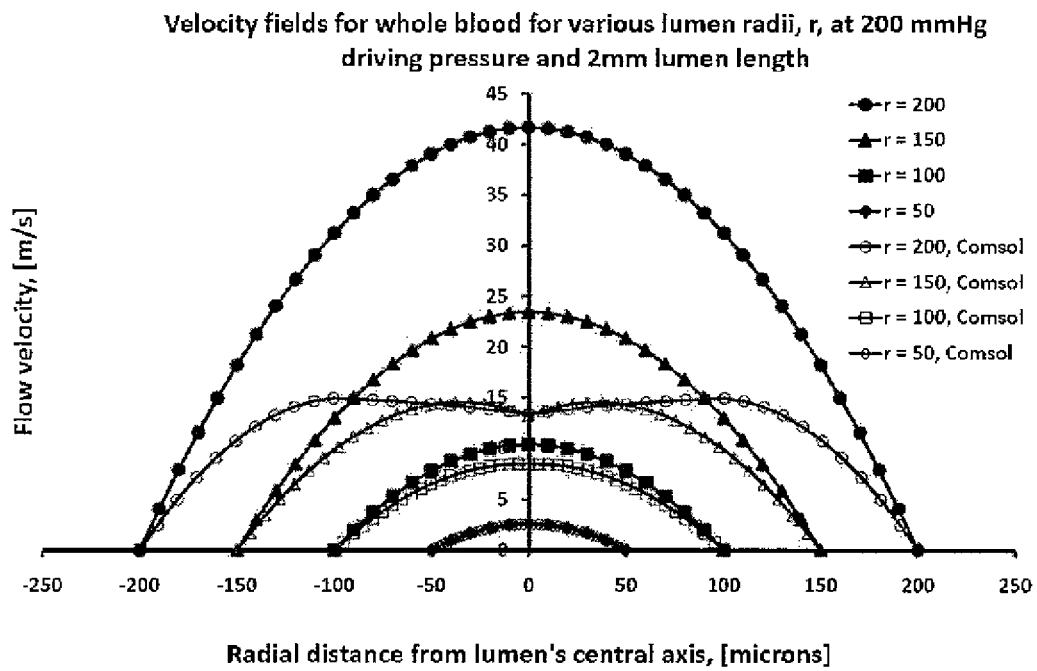
FIG. 4b is a graph illustrating velocity fields of circular Poiseuille flows through a practical implementation of an extroducer device.

FIG. 4b is a graph illustrating velocity fields of circular Poiseuille flows, filled symbols, [James A. Fay, Introduction to Fluid Mechanics, MIT Press, 1994, p 288.] through a practical implementation of an extroducer device according to an embodiment having a 2 mm long lumen, wherein the velocity fields of whole blood, at 37° C. and a physiological hematocrit of 45, driven by a pressure of 200 mmHg (Y-axis) are plotted against the r-coordinate (X-axis) for different lumen radius. Open symbols show calculations with a commercial programme, COMSOL Multiphysics, taking turbulent flow into account which reduces the velocity in the central part of the velocity fields when turbulent flow is present. For a radius of 50 micrometer, the result by COMSOL Multiphysics is identical to the circular Poiseuille flow, indicating full laminar flow for this geometry whereas the result by COMSOL Multiphysics is slightly reduced compared to the circular Poiseulle flow at a radius of 100 micrometer and heavily reduced at radii of 150 and 200 micrometer, respectively. The flow/lumen ratios determinable from the graph correspond to those of some embodiments of the extroducer device described herein.

Figure 5A:
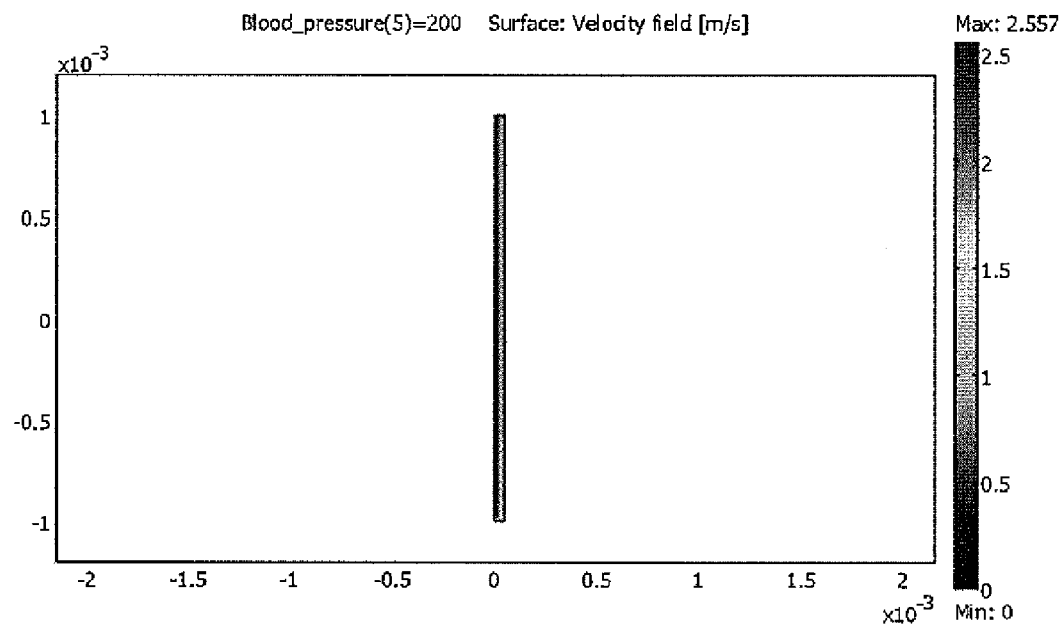
FIGS. 5A, 5B and 6A, 6B are graphs illustrating the velocity fields of flows of whole blood in two different communication channels.
Figure 5B:
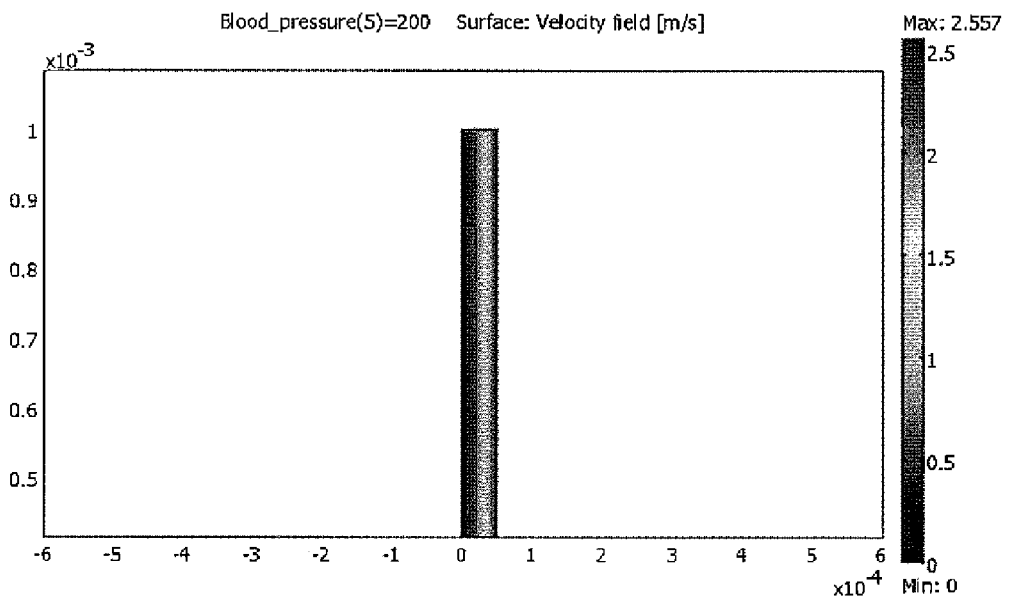
Figure 6A:
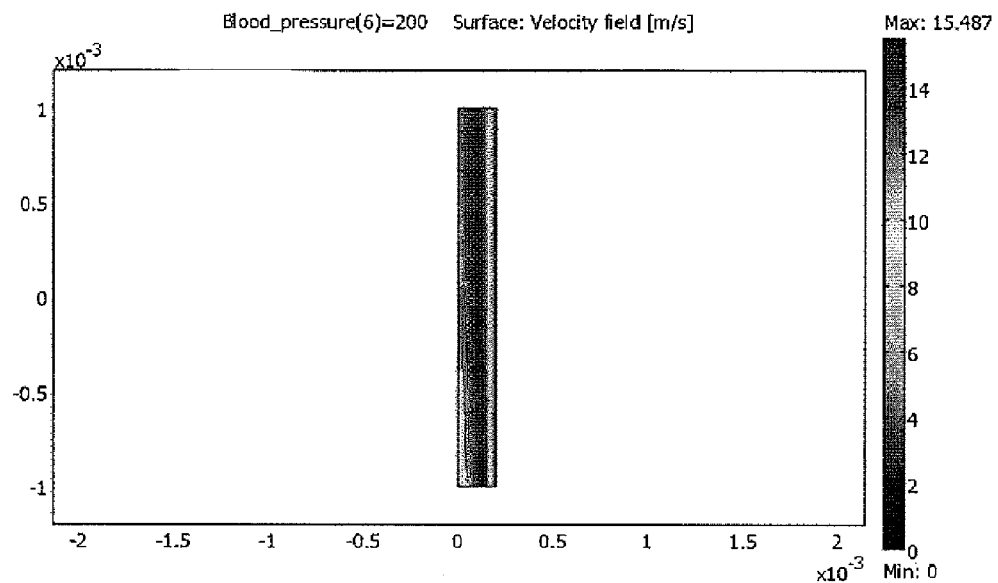
Figure 6B:
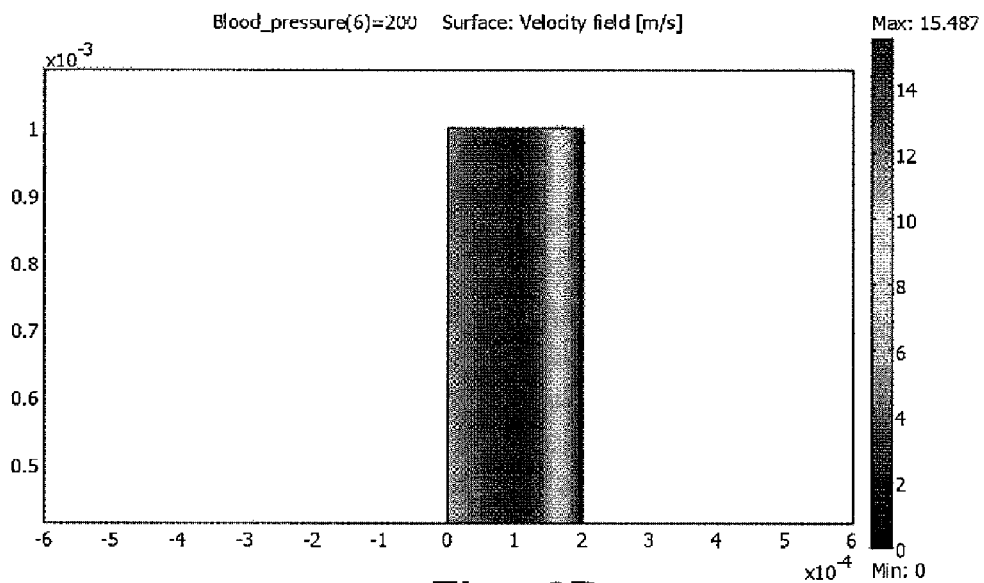

FIGS. 5A, 5B and 6A, 6B are graphs illustrating the velocity fields of flows of whole blood, at 37° C. and a physiological hematocrit of 45, driven by a pressure of 200 mmHg in two different communication channels of embodied devices having 50 and 200 micrometer radii, respectively, and a lumen length of 2 mm, simulated with a commercially available software product, COMSOL Multiphysics. FIGS. 5B and 6B show the upper 0.5 mm parts of FIG. 5A, 6A, respectively enlarged. The graphs are color coded, which in a black and white reproduction corresponds to different grey values in the figures. The figures show only half of the lumen, having positive coordinates, due to geometrical symmetry. The left border is a symmetry border, the bottom border is an inlet with an applied pressure of 200 mmHg, the right border is a non slip wall, and the upper border is an outlet with zero pressure. The lumen is filled with a liquid given a dynamic viscosity of 0.0032 Pas representing whole blood at 37° C. and a physiological hematocrit of 45. The velocity field is plotted and mapped by colour. As the graphs are color coded, a black and white reproduction corresponds to different grey values in the figures. The flow velocities determinable from the graphs correspond to those of some embodiments of the extroducer device described herein.

FIGS. 7A, 7B, 7C are a perspective view, a side view from above, and a lateral view of a practical implementation of an extroducer device 7 with an intrusion depth limitation unit and an attached microcatheter 3. The extroducer has a tapered part 102 ending at a hollow depth limiting part with a sudden increase in the radial dimension. The depth limiting part is attached to a hollow separation unit 115 allowing the extroducer to be detached from the micro catheter 3. The proximal portion 110 may comprise an inner hollow tube inside the microcatheter in fluid connection with the distal end 100. In an embodiment, the microcatheter 3 may act as the proximal portion 110, wherein the distal portion is attached to the microcatheter 3 by suitable means at the proximal convection section 101, such as by adhesive attachment, friction engagement, clamping, crimping, welding, soldering, etc. Preferably the attachment is made at the hollow separation unit 115, allowing for suitable detachment and separation of the distal portion 102 to be left in situ.

If dimension units are shown in the drawings of exemplary extroducer devices, the dimensions are given in mm. However, any dimensions given are not to be regarded as limiting entities.

FIGS. 8A, 8B, 8C are a perspective view, a side view from above, and a lateral view of another practical implementation of an extroducer device 8. The extroducer device 8 has a tapered part 102 ending at a hollow depth limiting part 116 with a sudden increase in the radial dimension (seen from the distal end). The depth limiting part 116 provides thus a shoulder element, is attached to a hollow separation unit 115 allowing the extroducer to be detached from the micro catheter 3, which in the present embodiment coincides with the proximal portion 110. Depth limiting part 116 is integrated with the hollow separation unit 115. The hollow separation unit 115 may be degradable, based on a spring effect, thermal detachment, etc. as described above.

FIGS. 9A, 9B, 9C are a perspective view, a side view from above, and a lateral view of a further practical implementation of an extroducer device 9. The extroducer device 9 has a elongate, tapered distal part 102 ending proximally at a hollow depth limiting part 116 with a foldable flange 118. The depth limiting part 116 is attached to the outside of the extroducer device 9. A hollow separation unit 115 allows the distal part 102 of the extroducer device 9 to be detached from the micro catheter 110.

FIGS. 10A, 10B, 10C are a perspective view, a side view from above, and a lateral view of yet another practical implementation of an extroducer device 10 with an intrusion depth limitation collar and a conical distal tip shape for easy accommodation in the vascular wall. The extroducer device 10 has an elongate, tapered part 102, proximally ending at a hollow depth limiting part 116 with a foldable flange 118. The depth limiting part 116 is attached to the outside of the extroducer. A hollow separation unit 115 allows the distal part 102 of the extroducer to be detached from the micro catheter 110. Compared to FIGS. 9A, 9B and 9C, the tapered part 102 is longer. Extroducer device 10 has a particularly advantageous dimension ratio to provide auto-sealing at physiological pressures for blood.

Figure 11C:
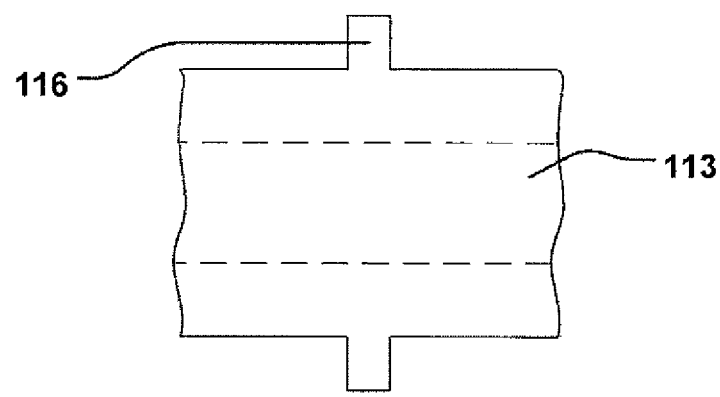

FIGS. 11A, 11B and 11C show in close views alternative configurations of an intrusion depth limiting unit. FIG. 11A and 11B illustrates two configurations with circumferential indentation, i.e. a waist appearance on the hollow body. FIG. 11C illustrates a flange configuration of the intrusion depth limiting unit where the adjacent structure of the unit is not tapered.

Figure 12A:
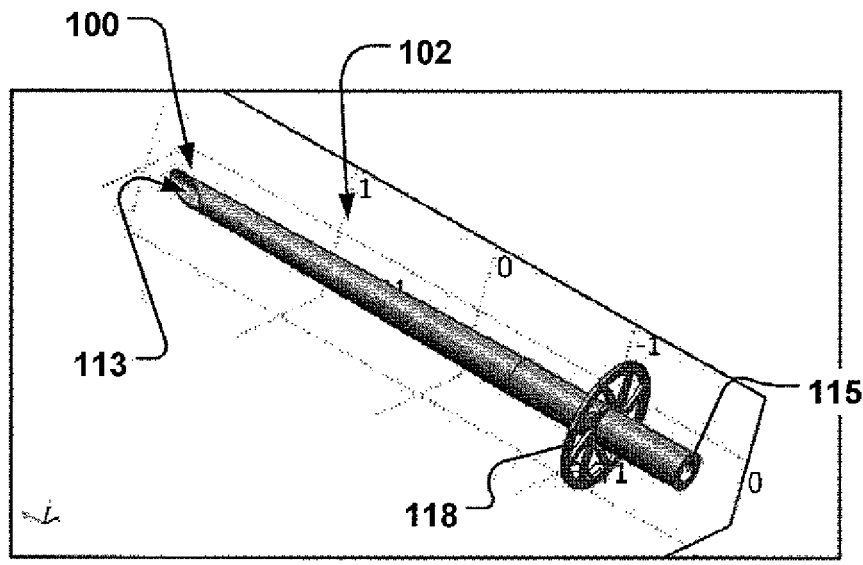
Figure 12B:
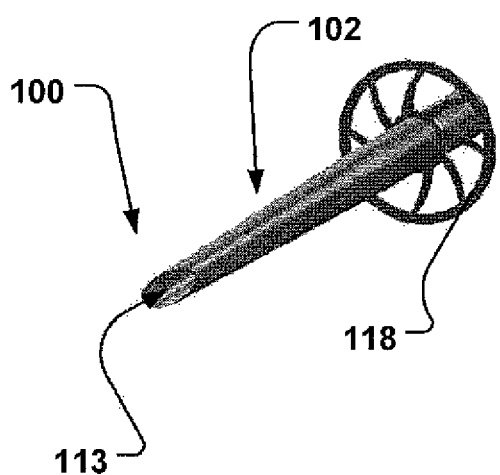

FIGS. 12A and 12B illustrate another intrusion depth limitation unit as a wheel formed flange. The flange is produced from a thin sheet of a highly flexible material as Nitinol by etching techniques based on photo lithography but not limited to these techniques. The flange 118 is attached to the exterior surface of the extruducer's lumen by press fitting, welding such as spot welding or laser welding or glued or by a combination of, but not limited to these methods. During advancement of the micro catheter system to the target site, the flange is folded forwards or backwards, between the exterior lumen surface of the extroducer or microcatheter and the interior surface of the polymer tube 2, forming the first assembly. The flange 118 is unfolded when the extroducer is advanced in the polymer tube 2 in order to perform a punctuation of a vasculatory wall. The flange is noninvasive due to lack of corners and is stress free in its unfolded position. The stiffness of the flange can be suitable adjusted by the width and thickness of the legs, blades, spokes, and the overall diameter of the wheel in relation to the outside diameter of the distal portion 102. The curved, and/or radially inclined, spokes facilitate the folding of the wheel when inserted into the polymer tube. It is possible to further assist folding by rotating the extroducer and micro catheter in the appropriate rotational direction, which can be an appropriate procedure if the extroducer is advanced out of the polymer tube at the target site and then, by any reason, the punctuation is interrupted and the whole system is being retracted. The illustrated flange has a thickness of 25 micrometer and a diameter of 0.80 mm.

Figure 13A:
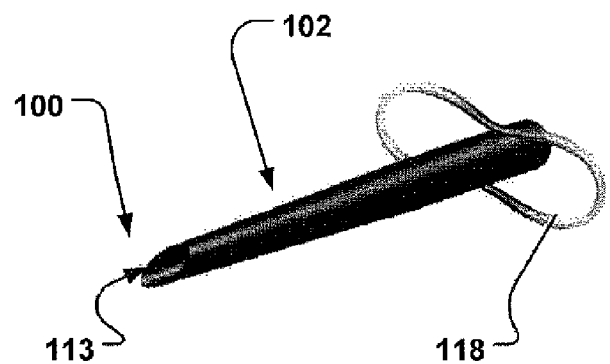
Figure 13B:
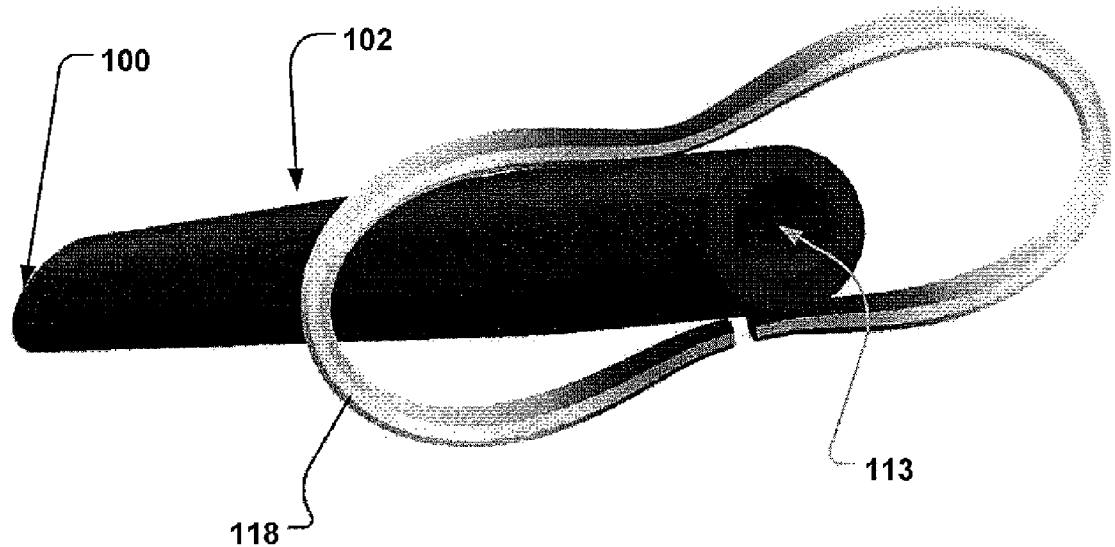

FIGS. 13A and 13B illustrate another intrusion depth limitation unit as a loop formed flange. The flange 118 is in this embodiment formed by attaching both ends of a highly flexible wire, such as a Nitinol wire, to the same side of the outer surface of the extroducer's outer body while the mid section of the wire is attached to the opposite side of the outer surface of said body. The attachment method can be one of the methods mentioned above or a combination of them. The illustration shows the von Mises stresses in a Nitinol wire of 44 micrometer circular cross sectional diameter originally shaped as a stress free circular loop of inner diameter 356 micrometer by first attaching the free wire ends to the extroducer and then pressing the circular loop against the extroducer on the opposite side, forming two wire loops extending from the extroducer. The stresses are color coded giving different grey levels in a black and white reproduction. The wire ends are practically stress free, whereas the highest stresses are found in the wire mid section pressed against the extroducer. During advancement of the micro catheter system to the target site, the flange is folded forwards or backwards, between the exterior lumen surface of the extroducer or micro-catheter and the interior surface of the polymer tube 2, forming the first assembly. The flange is unfolded when the extroducer is advanced in the polymer tube in order to perform a punctuation of a vasculatory wall. The design is non-invasive due to lack of sharp corners. The stiffness of the flanges can be adjusted by selecting different wire thicknesses and/or lengths. The two loops can preferably be oriented parallel to the blood vessel allowing a minimum intervention with the blood stream after the extroducer is detached from the micro catheter, being retracted, and left in position through the vasculatory wall. Thus, a flush arrangement of the detached proximal portion 102 is provided in a safe arrangement as blood pressure in the vessel will prevent a backward movement of the detached device into the vessel, and the flange 118 prevents a forward movement.

Figure 14A:
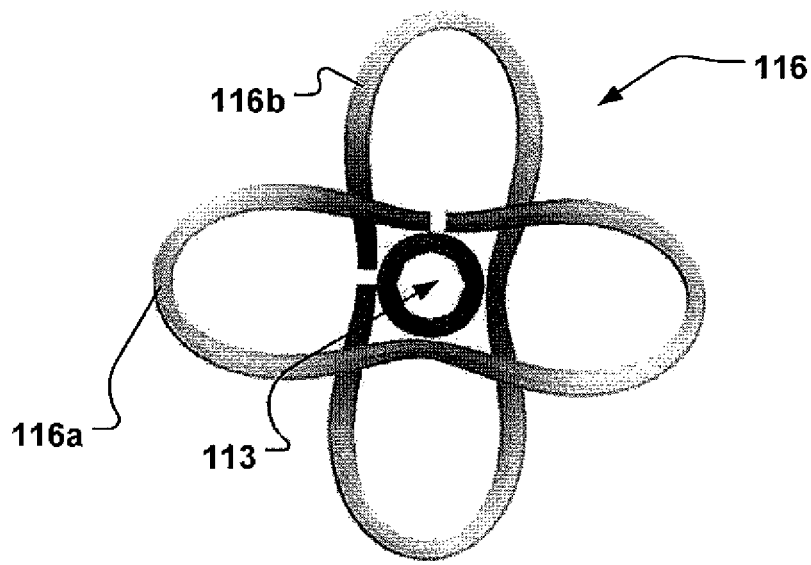
Figure 14B:
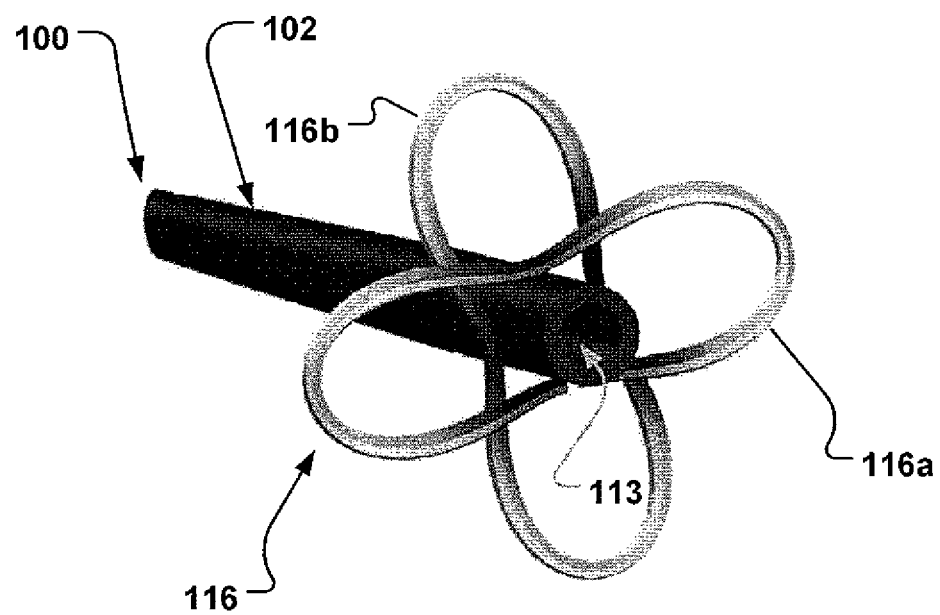
Figure 15A:
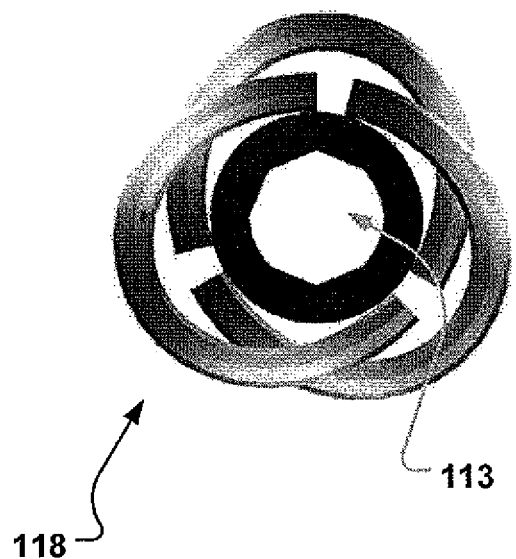
Figure 15B:
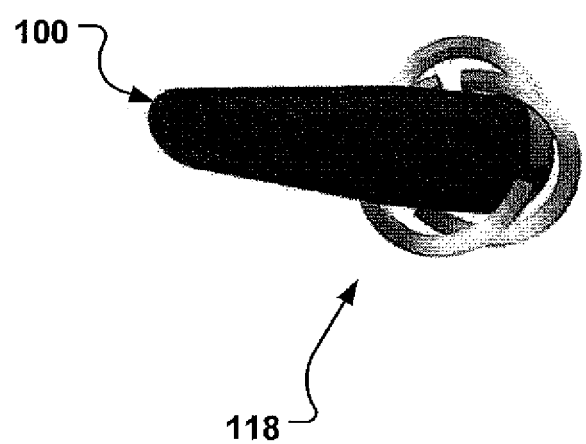
Figure 16A:
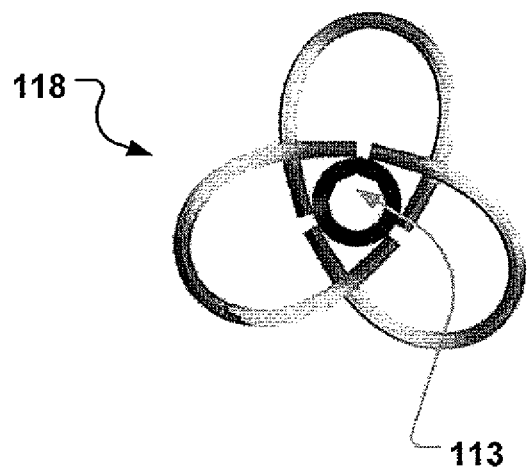
Figure 16B:
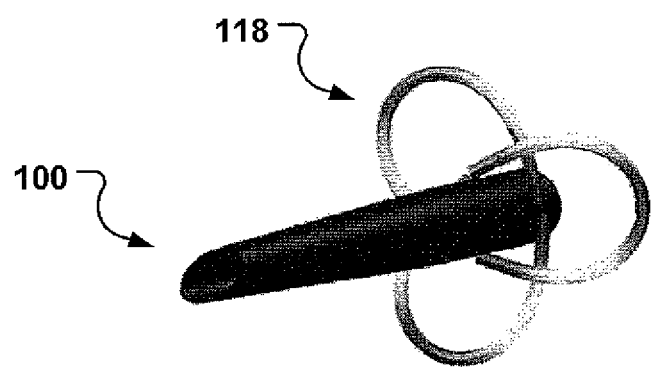

FIGS. 14A and 14B illustrate another intrusion depth limitation unit as a double loop formed flange of two loops 116a and 116b. Each pair of loops has the same dimensions, is formed, attached to the extroducer, folded during micro catheter advancement to the target site and unfolded prior to punctuation of the vasculatory wall, as described for FIGS. 13A and 13B. The increased number of loops allows an increased stiffness without selecting a thicker wire and hence allowing the use of finer micro catheter systems.

formed, attached to the extroducer, folded during micro catheter advancement to the target site and unfolded prior to punctuation of the vasculatory wall, as described for FIGS. 13A and 13B. The illustration shows an example constructed of three separate wires, but as an alternative, a single wire can be used to form the three loops of flange 118. The colors show the von Mises stresses in a Nitinol wire of 44 micrometer circular cross sectional diameter originally shaped as a stress free circular loop of inner diameter 300 micrometer simultaneously attaching the free wire ends to the extroducer on its opposite sides, forming a wire loop extending from the extroducer. The stresses are color coded giving different grey levels in a black and white reproduction. The stresses are more evenly distributed with the simultaneous deformation of the free wire ends than the method previously described starting with fixing only one wire end to the extroducer, then fixing the other free end and finally, fixing the mid section of the wire to the extroducer.

In alternative embodiments (not illustrated), the intrusion depth limitation unit may be provided as partial loops, or substantially straight radially extending protrusions, the distal ends thereof not returning to the attachment point on the extroducer device. Alternatively, or in addition, several of the described intrusion depth limitation units may be advantageously combined.

EXAMPLES

In Table 1, given below, typical dimensions of some embodiments are given.

TABLE 1

Typical dimension ranges and ratios of some embodiments of the extroducer

| dimensions in micrometers, approximal measures only | Length of distal portion 102 | Length of penetration limiter | Length of hollow detachment zone | Outer diameter | Lumen diameter | Flange diameter |
| --- | --- | --- | --- | --- | --- | --- |
| Min | Approx. 3× outer diameter of extroducer - 400-450 | a few micrometers - 10-20 | 0, if the catheter is dissolved no zone is needed | 140 | 100 | 300 |
| Max | No limit if it is made of a highly flexible material, such as nitinol. It must be possible to advance it through the vascular tree to the target site | Must not affect blood stream. Approx 0.3 times vessel diameter, - typically 250 micrometer | Limited by time/ energy amount of dissolved material. Process must not harm tissue. Smaller is better. Approx. 0.3 of vessel diameter, - typically 250 micrometer | Limited by polymer tube and micro catheter system, and intended target site | Limited by polymer tube and micro catheter system and intended target site | Limited by dimensions of the vessel. The wheel design is limited by the vessel diameter to approx. 1.5× of vessel diameter |
| dimensions in micrometers, approximal measures only | Total length of extroducer device before detachment | Ratio length/ diameter of distal portion 102 | Ratio length of distal portion 102/ total length before detachment | Ratio lumen diameter/length of distal portion 102 | | |
| Min | 100000 | 3 | 0.0042 | Depending on above dimensions, example: Range 0.03-0.1 For advant. Auto seal | | |
| Max | 1.50E+08 | undefined | unlimited | Depending on above dimensions, example: 0.25 | | |

FIGS. 15A, 15B, 16A, and 16B illustrate another intrusion depth limitation unit as a triple loop formed flange in respectively two different flange diameter versions. The loops are Several different practical implementations of the extroducer device were used to test different aspects in procedures designated for the extroducer device. The extroducer practical implementations described below and all consecutive steps of practical implementations were manufactured from a base of nitinol alloy tubes superelastic with an outer diameter 0.193 mm±0.0127 mm, inner diameter 0.104±0.0127 mm (Tube NiTi SE 508, ground surface, Euroflex GmbH, Pforzheim, Germany). However, these dimensions are not to be understood to be limiting and represent specific embodiments only.

The practical implementation A comprised a 29 cm long nitinol tube with a sharply cut end for perforating a vessel wall (FIG. 3B). Substances and cells were injected though the tube from the introducer end of the tube to the extroducer part located outside either the common carotid artery or the subclavian artery of the rat.

A further practical implementation B comprised a 2.5 mm long tube with a sharply cut end ground the same way as practical implementation A, and with an open lumen. The practical implementation B was advanced through a plastic microcatheter with a 29 cm long nitinol tube acting as a "pusher" for the practical implementation which was then inserted through the vascular wall.

In practical implementation C, a mechanical stop was added on the outer wall of the extroducer device. The mechanical stop was calibrated in size to determine the optimal radius in relation to the extroducer body to make an efficient stop for the extroducer during vascular penetration. This was first performed ex vivo by constructing a model of the human vasculature with its length and curves. At the distal end of this model rat vessels with different calibers were mounted and the practical implementation C, with different stop radii, was tested to determine the optimal stop to extroducer body ratio. The functionality of this stop radius was then tested in vivo in the rat. Thereafter, an expandable design of the chosen stop radius was developed and implemented to minimize the outer diameter of the system.

A hollow detachment zone was added for the extroducer practical implementation D, which was tested in vitro. During vascular penetration with practical implementation D, optionally a mandrel was inserted inside the extroducer to improve stability of the detachment zone.

A practical implementation E comprised a 170 cm long nitinol tube with a sharply cut end for perforating a vessel wall (compare with implementation A). The implementation E was tested in a rabbit model with full scale clinical routine guide- and micro-catheters and with angiography- and fluoroscopy-directed endovascular navigation.

As mentioned above, due to the small diameter of some embodiments of extroducer devices, there is no need for a lumen closure device before detachment. Physical principles prevent blood from inside the vessel (arteries and veins) to flow through the detached extroducer to the extravascular space. For larger diameter extroducers, closure of the working channel may be made as described and controlled with contrast injection before detachment. A small deformation/a small metal point was welded inside the lumen of the extroducer, to act as a stop for a metal (or silicon) plug pushed in place by a mandrel through the hollow body of the extroducer system.

The extroducer practical implementations A, B and C were introduced in the rat vascular system within a PTFE-160 Sub-lite wall tubing with outer diameter of 0.41±0.0254 mm and inner diameter of 0.25±0.0254 mm (AgnTho's, Sweden). Some of the practical implementation C prototypes with a solid stop was tested in an ex vivo model simulating the human vascular tree with perforation of a vessel specimen mounted at the distal end of the simulator model, introduced in the vascular system within a Sub-Lite wall tubing with a comparatively slightly larger outer as well as inner diameter, whereas the practical implementation C with expandable stop fitted into the smaller Sub-Lite wall tubing for in vivo testing. The practical implementation D was only tested in an in vitro system. The practical implementation E was introduced in the rabbit vascular system through a commercially available introducer and guide catheter and navigated within the vascular tree with a Prowler Plus microcatheter.

Extroducer—Design

When simulating water flow, with assistance of COMSOL Multiphysics, through the detached Extroducer (Prototype B and D) with an inner luminal diameter of such dimension that no laminar flow was observed with a driving pressure of 200 mm Hg (26.7 kPa) (FIG. 4a). This was also tested in vivo by rensing the transvascularly positioned open design extroducer practical implementations (B and D) with a nitinol mandrel. This was done to reassure that no clotting inside the practical implementation prevented bleeding from inside the vessel to the extravascular space. The test was performed in rats and there was no bleeding in any of the tested animals. However, when removing the entire prototype a major bleeding took place, hence confirming flow inside the vessel. This shows that, by providing that the distal portion of the extroducer device is separable from the proximal part, bleeding is effectively prevented when the distal portion is separated and left in place after the procedure.

The development of practical implementation C included testing of optimal stop to extroducer body ratio ex vivo. This ratio was then tested in vivo in rats and in all cases, the chosen stop radius made optimal positioning of the extroducer possible. The expandable version of the stop mechanism was tested in an identical fashion both ex vivo and in vivo.

Extroducer Device—Endovascular Testing

Small Animal Preparation

All animal experiments were conducted according to guidelines from the regional ethics committee for animal research at the Karolinska University Hospital, Stockholm, Sweden.

Male Sprague-Dawley rats (BW 240-350 g; B&K Universal AB, Stockholm, Sweden) were included in the study. Rats were divided into three groups to test the different practical implementations of the extroducer.

In group 1 (280-330 g) intervention was performed with practical implementation A. Directly following intervention, vessels were sampled and animals euthanatized. Group 2 (220-260 g) underwent intervention with practical implementation B, group 3 (220-240 g) with practical implementation C. Following intervention in group 2-3, the animals were sutured and allowed to recover in home cages. Animals in the groups 2-3 were sacrificed 14 days after insertion of the extroducer. Non-successful navigation animals of the subclavian or left common carotid artery were excluded from their groups and euthanized via decapitation under the same anesthesia session.

Surgical anesthesia was performed by an intramuscular (im) injection of 0.2 ml Hypnorm-Dormikum (1:1:2; Hypnorm (fentanyl citrate 0.315 mg/ml, fluanisone 10 mg/ml, Janssen Pharmaceutical, Beerse, Belgium): Dormikum (midazolam 1 mg/ml, Roche A B, Stockholm, Sweden)). Prior to skin incision, 0.1 ml Marcaine (5 mg/ml, Astra, Södertälje, Sweden) was injected subcutaneously in the area of operation. Animals were anesthetized with 0.1 ml Hypnorm im before decapitation.

Small Animal Surgical and Endovascular Procedures

All animal surgery was performed with a Leica M651 operating microscope coupled to a Sony CCD DXC930P camera. For operational video recording the CCD feed were streamed to a JVC SR-DVM70 DV/HDD/DVD recorder. Data was stored on DVD-R discs.

Introduction of catheters were performed via the medial tail artery. A small longitudinal incision was cut on the ventral part of the tail through the skin and the fascia overlying the artery. A ligature was used to secure the PTFE-160 tube containing a blunt nitinol tube and then the catheter system was blindly navigated up through the aorta.

For observation and usages of the extroducer practical implementations A-C, open surgical preparation of either the common carotid artery via a small mid-line incision medially on the neck, or the subclavian artery via an auxiliary exploration were performed. To maximize navigational success-rates both the major and the minor pectoral muscles were cut.

After navigation to exposed area with the blunted nitinol tube inside the PTFE-160 tube, the nitinol was exchanged for an extroducer practical implementation thereby protecting vessels from unplanned damage. After reaching tip to tip, the extroducer practical implementation was gently advanced through whatever vessel wall was closest taking advantage of the vessels non-linear anatomy. For all practical implementations, tests to exclude vasospasm as a potential hemostatic cause, were performed by soaking the perforated vessel with papaverin and observing for 90 minutes. Mechanical manipulation of the detached extroducer was also performed to provoke possible hemorrhage.

To be able to perform the intervention with simultaneous proximal balloon occlusion of the target vessel, the extroducer system was tested in conjunction with standard navigable balloon microcatheters. The diameter of the extroducer system made it possible to pass the entire system, including the protecting Sub-Lite tubing, inside standard balloon microcatheters.

Tissue Preparation

Following intervention animals in group 1, practical implementation A was gently retracted, vessels were clamped, cut and fixated in 4% buffered paraformaldehyde. Animals were then euthanatized via decapitation. In groups 2-3, animals were anesthetized 14 days after the first intervention and re-explored to the site of vascular perforation. Vessels were clamped, cut and fixated for 72 hours in 4% buffered paraformaldehyde at 4° C. Immediately following removal of vessels animals were euthanatized via decapitation.

Histochemistry

Vessels were placed in 15% sucrose following the fixation procedure for 24 hours at 4° C. The tissue was then mounted on a holder and frozen in a Leica cryostat (CM 3000, Leica Instruments GmbH, Nussloch, Germany). After freezing vessels to −24° C. they were covered with mounting medium and cut in 10 µm sections and then mounted onto Super Frost/Plus object glasses (Menzel-Gläzer, Braunschweig, Germany). Sections were stained with Hematoxylin and Eosin. Slides were then viewed with a Leica DM 4000 B and photographed with a coupled Leica DFC 320 CCD camera. Quantification of perforations in vascular walls was measured using ImageJ (Open-source software, NIH, Massachusetts, USA).

Large Animal Preparation

All animal experiments were conducted according to guidelines from the regional ethics committee for animal research at the Karolinska University Hospital, Stockholm, Sweden. Two male New Zealand White rabbits were included in the study. Surgical anesthesia was induced by subcutaneous injection of Hypnorm (fentanyl citrate 0.315 mg/ml, flu-anisone 10 mg/ml, Janssen Pharmaceutical, Beerse, Belgium) combined with diazepam. An intravenous line was established in the ear veins bilaterally. A bolus dose of Propofol was administered and thereafter, the rabbit was intubated with a size 3 pediatric tube and connected to a Siemens 900 servo ventilator. The animal was infused with propofol according to standard rabbit doses. In addition, 0.1 ml of Hypnorm was injected intravenously every 30 minutes.

Large Animal Surgical and Endovascular Procedures

The femoral artery of the anesthetized rabbit was exposed surgically and a 5 French Introducer was inserted in the vessel lumen (Terumo, USA). Under standard angiographic control, a 5 French Envoy guiding catheter (Cordis Corporation, USA) was advanced to different parts of the vasculature of the rabbit. A Prowler Plus microcatheter (Cordis Corporation, USA) was inserted within the Envoy guiding catheter and together with a Transend Platinum Tip guidewire (Boston Scientific, USA) navigated under angiographic control to the microvasculature (0.5-1 mm in lumen diameter) in different parts, including the central nervous system of the rabbit. The guidewire was withdrawn from the Prowler Plus microcatheter and the extroducer practical implementation E was introduced in the Prowler Plus microcatheter within a PTFE-160 Sub-Lite wall tubing with outer diameter of 0.41±0.0254 mm and inner diameter of 0.25±0.0254 mm (AgnTho's, Sweden).

Prototype A was tested on six animals with no case of intra-operative bleeding or intraluminal thrombosis. Thus, the vascular penetration procedure was uneventful and the vessel wall completely sealed around the extroducer and prevented leakage of blood. The vessel was exposed to papaverin to resolve potential vasospasm due to the penetration procedure and no bleeding or other complications were observed over a 90 minutes period. Histological analyses of vessels showed an average penetration diameter of 70 µm.

Prototype B was tested on seven animals again without any bleeding or other complications. Fourteen days post intervention, the group operated with practical implementation B followed their designated weight charts, showed no signs of pain or discomfort estimated by the Karolinska Institutet animal suffering template, from day 2 and onwards. No signs of impairment of blood-flow distal to intervention site were observed and histological analysis of the organ supplied by the vessel, showed no infarcts. Examination of vessels during re-exploration 14 days after the initial procedure, showed that they were viable without vessel dissections, with normal flow distal to the intervention site and with no signs of delayed hemorrhage. The extroducer practical implementation B was found associated to the outside vessel wall or in the extravascular space adjacent to the penetration site.

Prototype C was first evaluated ex vivo by penetrating vessel walls obtained from carcasses analyzing applied forces through a loading cell connected to the vessels. Calculations of force ratios between penetration with only the tip and perforation with intrusion limiting devices were conducted. With suitable diameters, the penetration of vessels in vivo was envisaged in all cases and the stop radius made optimal positioning possible in all cases. No complications such as bleeding, dissection or thrombosis were encountered. The results of the testing of the expandable stop design were identical to the results of the solid stop mechanism.

Prototype D evaluated in vitro one possible mechanism of dividing the distal penetrator end from the proximal access catheter without complication. A 29 cm long nitinol tube was ground at one end to produce a sharp tip, cleaned with alcohol and hung vertically, with the sharp tip pointing down, on a twistable shaft. The whole tube was spray painted from four perpendicular directions with a blanc white acrylic paint, CRC Pro Paint (Clas Ohlsson, Sweden) and left to dry at room temperature for an hour. A stainless steel tube with inner diameter 310 micrometer, outer diameter 800 micrometer and length 10 mm was carefully threaded on the painted catheter without damaging the paint. A circumferential cut in the paint was made approximately 2 mm from the sharp tip and adjacent to the stainless steel tube. An electrode was attached to the stainless steel tube and about 5 cm of the catheter was submerged into a physiological salt solution leaving only the electrode and,catheter sticking out of the solution. A voltage of 7V was applied by an external electrical source between the electrode (cathode) and the catheter (anode) resulting in a circumferential dissolution of the catheter where the cut in the paint was made. The distal penetration end was then separated from the proximal access portion of nitinol tube.

The extroducer practical implementation E was tested for its ability to penetrate the vessel wall in different parts of the microvasculature. Thus, these experiments were designed to fully simulate the clinical situation and thereby make analysis of the compatibility and behaviour of the extroducer system possible.

The extroducer practical implementations were constructed in Nitinol and tested ex vivo in a simulator and in vivo in the rat and rabbit. The extroducer consists of a single lumen long flexible tube connected with a hollow detachment zone to a vascular penetration device at the distal end. The device is protected inside a microsilicon tubing during navigation to the desired location. At the junction between the detachment zone and the penetration device, there is an expandable stop which makes optimal positioning of the system possible with fluoroscopy. The dimension of the system can be varied according to the vascular dimensions in the target organ. For small inner lumen diameters, physical laws prevent blood from flowing from the inside to out through the detached distal part. For larger inner lumen diameter, a plug of suitable material, such as metal or silicon, is advanced through the tube to the distal part to seal off the lumen before detachment. Sealing is confirmed with contrast injection under X-ray exposure. Catheterization of rat arteries was made via the medial tail artery up to the left subclavian or common carotid artery where exit of the vascular system was performed (n=40). Catheterization of the veins was made via suitable access veins up to vein were exit was performed. Surgical exposure was performed at the site of vascular entry in the tail and at the site of exit in the neck or in the axilla. The vessels and tissues were analyzed in the acute phase and after 14 days.

To test the feasibility of one possible application, namely a cell transplantation procedure, cell suspensions were injected through the nitinol catheter and distal extroducer lumen. These tests were performed in a system with the smallest lumen diameter available (ID 0.104±0.0127 mm).

Results

Interventions have been performed in the rat by introduction of catheters through the medial tail artery and testing extroducer practical implementations in either the subclavian artery or the common carotid artery on the left side. Interventions have also been performed in the rabbit by introduction of catheters through the femoral artery using standard clinical introducers, guiding catheters and microcatheters and wires.

Five different developmental steps of the extroducer were tested, named practical implementations A-E. The implementations A-C and E, all demonstrated absolute extravascular hemostasis and absence of thromboembolic complications when exiting the artery or vein from the inside to out, whereas implementation D was tested in vitro.

Extroducer practical implementations B were placed in vascular walls over a period of 14 days with no impairment on blood flow upon re-exploration.

Practical implementation E further showed full compatibility with the full clinical setting with fully preserved functionality from small animal testing hence verifying the concept of a fully operational kit, deployable for standard use. The penetration of the vascular wall was easily performed in 100% of the attempts (n=20). The two animals were sacrificed immediately after the experiments. The rabbit experiments thereby demonstrated that the extroducer system functions in a standard angiographic environment and with standard, clinically available, introducers, guiding catheters and microcatheters.

The evaluation of one possible application, i.e. cell transplantation via the smallest available lumen diameter showed that 10% of the cells died due to passage, but the remaining 90% of the cells survived and were possible to passage in vitro again. Injection of other substances with normal viscosity through the catheter system and extroducer worked without any problem. This was also demonstrated in vivo by deposition of Methylene Blue in the extravascular space of the rat through the extroducer system.

Results of the Examples

Tests of the system was performed in an ex vivo system simulating the size and tortuisity of human vasculature. The whole system is easily placed within standard microcatheter systems. Rat vessels of different sizes were mounted at the distal end of the simulator to optimize the design of the distal part of the extroducer. After exiting the artery or the vein from the inside to out, cells or substances could be injected into the extravascular space and thereafter the distal part was detached, leaving it through the vessel wall with only the minute stop mechanism present adjacent to the vessel wall on the separated distal end of the extroducer. No complications such as bleeding, dissections or thromboembolic complications were encountered, neither in the acute phase, nor after 14 days.

Conclusion: A system for injection or sampling of cells or substances in any organ throughout the body by using the endovascular route is provided. The design of the system makes navigation and exit of also the microvasculature possible on both the arterial and venous side. The potential applications for the system are numerous, for example stem cell transplantation to organs difficult to reach by puncture or open surgery, such as the central nervous system, the pancreas or the heart.

Extroducer practical implementations novel design has sustained all testing without bleeding. It is a novel way of applying endovascular intervention aimed at transplantation of cell cultures, delivering drugs and possibly sampling body fluids and cytological preparations. The entire system fits into current standard catheter systems eliminating the need for navigation with the extroducer system and easily integrating it with current standard equipment.

The present invention has been described above with reference to specific embodiments. However, other embodiments than the above described are equally possible within the scope of the invention. Different method steps than those described above, performing the method by hardware or software, may be provided within the scope of the invention. The different features and steps of the invention may be combined in other combinations than those described. The scope of the invention is only limited by the appended patent claims.

The invention claimed is:

1. An endoluminal medical access device, devised for endoluminal delivery to an extravascular target site at a vasculature site of a human or animal body vasculature, wherein said device comprises:
   a hollow body that is arranged around a continuous channel that ends in an opening at a distal end of said device; wherein said hollow body comprises:

a detachable elongate distal portion that is configured to perforate a tissue wall of said vasculature at said vasculature site in said body, to provide communication with said extravascular target site through said channel, and for positioning at least partly in apposition to said tissue wall, and a proximal portion, which proximally adjoins said distal portion at a proximal connection section; and a hollow separation section that is arranged at said hollow body for controlled separation of said distal portion from said proximal portion of said hollow body at said proximal connection section while said distal elongate portion is at least partly in apposition to said tissue wall to provide said communication with said extravascular target site through said channel.

2. The endoluminal medical access device according to claim 1, wherein said detachable elongate distal portion has a sharp tissue penetration tip at said distal end.

3. The endoluminal medical access device according to claim 1, wherein said hollow separation section is adapted to provide a connection of said proximal portion and said distal penetration portion during delivery to said vasculature site and a subsequent pre-defined time for fluid communication through said channel and facilitates separation of said proximal connection section and said distal penetration portion from each other following said pre-defined time.

4. The endoluminal medical access device according to claim 1, wherein said hollow separation section is configured to provide said controlled separation based on electrolytic, magnetic, induction or thermal detachment, spring force release, at least one predetermined breaking point, threaded detachment, or cutting rotational movement, for separation of said distal penetration portion from said proximal connection section.

5. The endoluminal medical access device according to claim 1, comprising an intrusion depth limitation unit for preventing introduction of said distal penetration portion beyond a desired insertion depth in said vascular wall,
wherein said hollow separation section is arranged proximally said intrusion depth limitation unit and thus arranged to separate together with said distal penetration portion from said proximal connection section.

6. The endoluminal medical access device according to claim 5, wherein said intrusion depth limit unit is a retention unit comprising a flange devised to limit an intrusion depth of said endoluminal medical access device into said tissue wall, or wherein said intrusion depth limit unit is a retention unit comprising a flange devised to limit an intrusion depth of said endoluminal medical access device into said tissue wall and wherein said flange is foldable towards said hollow body; or wherein said intrusion depth limit unit is a recess in an outer wall of said hollow body.

7. The endoluminal medical access device according to claim 1, wherein said elongate distal penetration portion is tapered towards said distal end.

8. The endoluminal medical access device according to claim 1, wherein said channel at said distal portion has an inner diameter to length ratio such that said distal portion is auto sealing for blood flow at physiological pressures, whereby said device is adapted for delivery either in an arterial or a venous side of said vasculature.

9. The endoluminal medical access device according to claim 8, wherein said ratio of said lumen diameter to said length of said distal portion is in the range of 0.03 to 0.1.

10. The endoluminal medical access device according to claim 1, wherein a ratio of a length of said distal portion to a total length of said device before detachment of said distal portion is at least 0.0042.

11. The endoluminal medical access device according to claim 1, wherein said endoluminal medical access device is adapted to be sealed by a sealing plug when advanced through the hollow body of the endoluminal medical access device to the distal detachable portion when the latter is left in a vessel wall at the vasculature site.

12. The endoluminal medical access device according to claim 1, wherein said hollow body is a hollow tube, and a material of said hollow body is a bio-compatible material.

13. The endoluminal medical access device according to claim 1, wherein a material of distal portion is a bioresorbable or biodegradable material.

14. The endoluminal medical access device according to claim 1, wherein said endoluminal medical access device is adapted to fit into a standard larger catheter for delivery to a site remote of said target site and further a microcatheter coaxially inside said catheter for delivery to a neighbouring microvasculature site.

15. A kit comprising an endoluminal medical access device according to claim 1, and a first elongated tubular delivery device.

16. The kit according to claim 15, wherein said first elongated tubular delivery device is a tubing of polymeric material arranged coaxially around said endoluminal medical access device, providing a first assembly, wherein the latter is arranged for sliding motion in said tubing.

17. The kit according to claim 16, wherein said first assembly is coaxially arranged for sliding motion in a microcatheter.

18. A method of endoluminal access to an extravascular target site at a vasculature site in a human or animal body, comprising using an endoluminal device, said endoluminal device comprising:
a hollow body that is arranged around a continuous channel that ends in an opening at a distal end of said device; wherein said hollow body comprises:
a detachable elongate distal portion that is devised to extend across a tissue wall of said vasculature at said vasculature site in said body and devised to provide communication with said extravascular target site through said channel and devised for positioning at least partly in apposition to said tissue wall, and
a proximal portion, which proximally adjoins said distal portion at a proximal connection section; and
a hollow separation section that is arranged at said hollow body for controlled separation of said distal portion from said proximal portion of said hollow body at said proximal connection section while said distal elongate portion is at least partly in apposition to said tissue wall to provide said communication with said extravascular target site through said channel,
said method comprising:
perforating a vessel wall of said vasculature at an extravascular target site in said body, and positioning a distal portion of said device extending across said vessel wall at least partly in apposition to said tissue wall, and providing communication with an extravascular space at said target site through a communication channel in said device,
detaching said distal portion from a proximal portion and leaving said distal portion in said vessel wall after a procedure, and removing a proximal connection section of said device from said body.

19. The method according to claim 18, wherein said perforating is made with a sharp tip at a distal end of said distal portion.

20. The method according to claim 18, wherein said distal portion after said detaching is auto sealing for blood flow at physiological pressures in said vessel.

21. A method of communicating with a target site in an animal or human body, said method comprising establishing communication with said target site by performing the method according to claim 18, wherein said procedure is delivery of a substance to said target site or taking of a sample from said target site through said communication channel, wherein said delivery or taking of sample is made at a pressure higher than a physiological pressure in said vessel.

22. The method according to claim 21, wherein said substance comprises cells thus endovascularly transplanting said cells into said target site.

23. The method according to claim 21, wherein said delivery of a substance comprises local administration of said substance.

24. The method according to claim 21, wherein said taking of said sample comprises a puncture of a cyst.

25. The method according to claim 21, further comprising subintimally passing an occlusion or stenosis of a vessel with said device.

* * * * *

UNITED STATES PATENT AND TRADEMARK OFFICE
CERTIFICATE OF CORRECTION

PATENT NO. : 8,876,792 B2  
APPLICATION NO. : 12/936825  
DATED : November 4, 2014  
INVENTOR(S) : Holmin et al.

Page 1 of 1

It is certified that error appears in the above-identified patent and that said Letters Patent is hereby corrected as shown below:

In the Specification

Column 3 line 65, Change "trough" to --through--.

Column 4 line 46, Change "seperable" to --separable--.

Column 10 line 65, Change "eximer" to --excimer--.

Column 12 line 13, Change "Range" to --Flange--.

Column 14 line 24, Change "dement," to --element,--.

Column 16 line 66, Change "Poiseulle" to --Poiseuille--.

Column 17 line 39, Change "convection" to --connection--.

Column 23 line 51, Change "Gläzer," to --Gläser,--.

Column 24 line 13, Change "Transend" to --Transcend--.

Column 24 line 62, Change "twistable" to --twisteable--.

Column 24 line 64, Change "Ohlsson," to --Ohlson,--.

Column 25 line 6, Change "and,catheter" to --and catheter--.

Column 26 line 20, Change "tortuisity" to --tortuosity--.

Signed and Sealed this  
Twenty-sixth Day of May, 2015

Michelle K. Lee  
*Director of the United States Patent and Trademark Office*